US009562075B2

(12) United States Patent
Van Der Burg et al.

(10) Patent No.: US 9,562,075 B2
(45) Date of Patent: Feb. 7, 2017

(54) INTRADERMAL HPV PEPTIDE VACCINATION

(75) Inventors: Sjoerd Henricus Van Der Burg, Leiden (NL); Gemma G. Kenter, Amsterdam (NL); Cornelis Johannes Maria Melief, Haarlem (NL)

(73) Assignee: Academisch Ziekenhuis Leiden H.O.D.N. LUMC, Leiden (NL)

( * ) Notice: Subject to any disclaimer, the term of this patent is extended or adjusted under 35 U.S.C. 154(b) by 544 days.

(21) Appl. No.: 12/451,983

(22) PCT Filed: May 27, 2008

(86) PCT No.: PCT/NL2008/050315
§ 371 (c)(1),
(2), (4) Date: Apr. 12, 2010

(87) PCT Pub. No.: WO2009/002159
PCT Pub. Date: Dec. 31, 2008

(65) Prior Publication Data
US 2010/0196353 A1    Aug. 5, 2010

Related U.S. Application Data

(60) Provisional application No. 60/941,070, filed on May 31, 2007.

(30) Foreign Application Priority Data

May 31, 2007 (EP) ..................... 07109287

(51) Int. Cl.
*A61K 39/12* (2006.01)
*C07K 14/005* (2006.01)
*C12N 7/00* (2006.01)
*A61K 39/00* (2006.01)

(52) U.S. Cl.
CPC ............ *C07K 14/005* (2013.01); *A61K 39/12* (2013.01); *C12N 7/00* (2013.01); *A61K 2039/54* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| | | | |
|---|---|---|---|
| 4,777,239 A * | 10/1988 | Schoolnik et al. | 530/326 |
| 5,401,627 A * | 3/1995 | Dillner et al. | 435/5 |
| 5,665,533 A | 9/1997 | Hopfl et al. | |
| 5,932,412 A | 8/1999 | Dillner et al. | |
| 6,096,869 A * | 8/2000 | Stanley et al. | 530/351 |
| 6,419,931 B1 | 7/2002 | Vitiello et al. | |
| 7,202,034 B2 * | 4/2007 | Van Der Burg et al. | 435/6.14 |
| 7,399,467 B2 | 7/2008 | Lu et al. | |
| 7,659,071 B2 * | 2/2010 | Sastry et al. | 435/6.14 |
| 7,807,369 B2 * | 10/2010 | van der Burg et al. | 424/155.1 |
| 8,252,893 B2 | 8/2012 | Kim et al. | |
| 2001/0029022 A1 | 10/2001 | Fisher et al. | 435/7.1 |
| 2002/0044948 A1 | 4/2002 | Khleif et al. | 424/234.1 |
| 2003/0029461 A1 | 2/2003 | Hermonat et al. | 128/898 |
| 2004/0081658 A1 * | 4/2004 | Van Der Burg et al. | 424/185.1 |
| 2005/0048467 A1 * | 3/2005 | Sastry et al. | 435/5 |
| 2009/0028874 A1 * | 1/2009 | Van Der Burg et al. | 424/172.1 |

FOREIGN PATENT DOCUMENTS

| | | |
|---|---|---|
| WO | WO 97/23237 | 7/1997 |
| WO | WO-02/070006 A2 | 9/2002 |
| WO | WO-03/084999 A1 | 10/2003 |
| WO | WO 2006/115413 | * 11/2006 |
| WO | WO 2007/006939 | 1/2007 |

OTHER PUBLICATIONS

Van Der Burg et al, In. J. Cancer, 2001, vol. 91, pp. 612-618.*
Zwaveling S et al. Established human papillomavirus type 16-expressing tumors are effectively eradicated following vaccination with long peptides. J Immunol. Jul. 1, 2002;169(1):350-8.*
Hopfl et al. Spontaneous regression of CIN and delayed-type hypersensitivity to HPV-16 oncoprotein E7. The Lancet, 2000, 356:1985-1986.*
Zwaveling et al. J Immunol. Jul. 1, 2002;169(1 ):350-8.*
Peng et al. HLA-DQB1*02-restricted HPV-16 E7 peptide-specific CD4+ T-cell immune responses correlate with regression of HPV-16-associated high-grade squamous intraepithelial lesions. Clin Cancer Res. Apr. 15, 2007;13(8):2479-87.*
Villada et al. Identification in humans of HPV-16 E6 and E7 protein epitopes recognized by cytolytic T lymphocytes in association with HLA-B18 and determination of the HLA-B18-specific binding motif. Eur. J. Immunol. 2000. 30: 2281-2289.*
Rahman et al. Cellular and Humoral Immune Responses Induced by Intradermal or Intramuscular Vaccination With the Major Hepatitis B Surface Antigen. Hepatology 2000;31:521-527.*
Peter L. Stern. Immune control of human papillomavirus (HPV) associated anogenital disease and potential for vaccination. Journal of Clinical Virology 32S (2005) S72-S81.*
GenBank: AAV91677.1. E7 [Human papillomavirus type 16], dated May 21, 2005.*
GenBank: AAV91684.1. E6 [Human papillomavirus type 16], dated May 21, 2005.*
GenBank: AAQ10406.1. E2 [Human papillomavirus type 16], dated Sep. 1, 2003.*
Ludewig et al. In vivo antigen loading and activation of dendritic cells via a liposomal peptide vaccine mediates protective antiviral and anti-tumour immunity. Vaccine 19 (2001) 23-32.*

(Continued)

*Primary Examiner* — Nick Zou
(74) *Attorney, Agent, or Firm* — Foley & Lardner LLP; Sunit Talapatra

(57) ABSTRACT

The invention relates to the use of a peptide derived from HPV-E2, E6 and/or E7 protein for the manufacture of a medicament for the treatment or prevention of an HPV related disease, wherein the medicament is for intradermal administration.

12 Claims, 4 Drawing Sheets

(56) References Cited

OTHER PUBLICATIONS

Qian et al. Combined prophylactic and therapeutic cancer vaccine: Enhancing CTL responses to HPV16 E2 using a chimeric VLP in HLA-A2 mice. Int. J. Cancer: 118, 3022-3029 (2006).*

Welters et al. Frequent display of human papillomavirus type 16 E6-specific memory t-Helper cells in the healthy population as witness of previous viral encounter. Cancer Res. Feb. 1, 2003;63(3):636-41.*

Chen et al. Characterization of antigen-specific CD8+ T lymphocyte responses in skin and peripheral blood following intradermal peptide vaccination. Cancer Immun. Mar. 9, 2005;5:5.*

Disis et al. Generation of immunity to the HER-2/neu oncogenic protein in patients with breast and ovarian cancer using a peptide-based vaccine. Clin Cancer Res. Jun. 1999;5(6):1289-97.*

Knight et al. A peptide of Chlamydia trachomatis shown to be a primary T-cell epitope in vitro induces cell-mediated immunity in vivo. Immunology. May 1995;85(1):8-15.*

Zwaveling et al., "Established Human Papillomavirus Type 16-Expressing Tumors Are Effectively Eradicated Following Vaccination with Long peptides", J of Immunology, vol. 169, No. 1, Jul. 1, 2002, pp. 350-358.

Vambutas et al., "Therapeutic vaccination with papillomavirus E6 and E7 long peptides results in the control of both established virus-induced lesions and latently infected sites in a pre-clinical cottontail rabbit papillomavirus model", Vaccine, vol. 23, No. 45, Nov 1, 2005, pp. 5271-5280.

Brandsma et al., "Vesicular Stomatitis Virus-Based Therapeutic Vaccine Targeted to the E1, E2, E6 and E7 Proteins of Cottontail Rabbit Papillomavirus", J of Virology, vol. 81, No. 11, Jun. 2007, pp. 5749-5758.

Dillion et al., "Resolution of cervical dysplasia is associated with T-cell proliferative response to human papillomavirus type 16 E2", J of General Virology, vol. 88, No. Pt 3, Mar. 2007, pp. 803-813.

Hopfl et al, "Skin test for HPV type 16 proteins in cervical intraepithelial neoplasia", LANCET, vol. 337, No. 8737, Feb 9, 1991, pp. 373-374.

Han, et al. "Protection of Rabbits from Viral Challenge by Gene Gun-Based Intracutaneous Vaccination with a Combination of Cottontail Rabbit Papillomavirus EI, E2, E6, and E7 Genes", Journal of Virology, (Aug. 1999), vol. 73, No. 8, pp. 7039-7043.

* cited by examiner

SEQUENCE LISTING

<160> NUMBER OF SEQ ID NOS: 23

<210> SEQ ID NO 1
<211> LENGTH: 365
<212> TYPE: PRT
<213> ORGANISM: Human papillomavirus

<400> SEQUENCE: 1

```
Met Glu Thr Leu Cys Gln Arg Leu Asn Val Cys Gln Asp Lys Ile Leu
1               5                   10                  15

Thr His Tyr Glu Asn Asp Ser Thr Asp Leu Arg Asp His Ile Asp Tyr
                20                  25                  30

Trp Lys His Met Arg Leu Glu Cys Ala Ile Tyr Tyr Lys Ala Arg Glu
            35                  40                  45

Met Gly Phe Lys His Ile Asn His Gln Val Val Pro Thr Leu Ala Val
        50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
    210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
```

```
                         245                 250                 255
Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
            275                 280                 285

Val His Leu Lys Gly Asp Ala Asn Thr Leu Lys Cys Leu Arg Tyr Arg
            290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
            355                 360                 365

<210> SEQ ID NO 2
<211> LENGTH: 158
<212> TYPE: PRT
<213> ORGANISM: Human papillomavirus

<400> SEQUENCE: 2

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 3
<211> LENGTH: 98
<212> TYPE: PRT
<213> ORGANISM: Human papillomavirus

<400> SEQUENCE: 3

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
```

```
Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 4
<211> LENGTH: 365
<212> TYPE: PRT
<213> ORGANISM: Human papillomavirus

<400> SEQUENCE: 4

Met Gln Thr Pro Lys Glu Thr Leu Ser Glu Arg Leu Ser Cys Val Gln
1               5                   10                  15

Asp Lys Ile Ile Asp His Tyr Glu Asn Asp Ser Lys Asp Ile Asp Ser
                20                  25                  30

Gln Ile Gln Tyr Trp Gln Leu Ile Arg Trp Glu Asn Ala Ile Phe Phe
            35                  40                  45

Ala Ala Arg Glu His Gly Ile Gln Thr Leu Asn His Gln Val Val Pro
50                  55                  60

Ala Tyr Asn Ile Ser Lys Ser Lys Ala His Lys Ala Ile Glu Leu Gln
65                  70                  75                  80

Met Ala Leu Gln Gly Leu Ala Gln Ser Arg Tyr Lys Thr Glu Asp Trp
                85                  90                  95

Thr Leu Gln Asp Thr Cys Glu Glu Leu Trp Asn Thr Glu Pro Thr His
            100                 105                 110

Cys Phe Lys Lys Gly Gly Gln Thr Val Gln Val Tyr Phe Asp Gly Asn
            115                 120                 125

Lys Asp Asn Cys Met Thr Tyr Val Ala Trp Asp Ser Val Tyr Tyr Met
130                 135                 140

Thr Asp Ala Gly Thr Trp Asp Lys Thr Ala Thr Cys Val Ser His Arg
145                 150                 155                 160

Gly Leu Tyr Tyr Val Lys Glu Gly Tyr Asn Thr Phe Tyr Ile Glu Phe
                165                 170                 175

Lys Ser Glu Cys Glu Lys Tyr Gly Asn Thr Gly Thr Trp Glu Val His
            180                 185                 190

Phe Gly Asn Asn Val Ile Asp Cys Asn Asp Ser Met Cys Ser Thr Ser
            195                 200                 205

Asp Asp Thr Val Ser Ala Thr Gln Leu Val Lys Gln Leu Gln His Thr
210                 215                 220

Pro Ser Pro Tyr Ser Ser Thr Val Ser Val Gly Thr Ala Lys Thr Tyr
225                 230                 235                 240

Gly Gln Thr Ser Ala Ala Thr Arg Pro Gly His Cys Gly Leu Ala Glu
                245                 250                 255

Lys Gln His Cys Gly Pro Val Asn Pro Leu Leu Gly Ala Ala Thr Pro
            260                 265                 270

Thr Gly Asn Asn Lys Arg Arg Lys Leu Cys Ser Gly Asn Thr Thr Pro
            275                 280                 285

Ile Ile His Leu Lys Gly Asp Arg Asn Ser Leu Lys Cys Leu Arg Tyr
            290                 295                 300

Arg Leu Arg Lys His Ser Asp His Tyr Arg Asp Ile Ser Ser Thr Trp
305                 310                 315                 320

His Trp Thr Gly Ala Gly Asn Glu Lys Thr Gly Ile Leu Thr Val Thr
```

```
                    325                 330                 335
Tyr His Ser Glu Thr Gln Arg Thr Lys Phe Leu Asn Thr Val Ala Ile
                340                 345                 350

Pro Asp Ser Val Gln Ile Leu Val Gly Tyr Met Thr Met
                355                 360                 365

<210> SEQ ID NO 5
<211> LENGTH: 158
<212> TYPE: PRT
<213> ORGANISM: Human papillomavirus

<400> SEQUENCE: 5

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
130                 135                 140

Ala Arg Gln Glu Arg Leu Gln Arg Arg Glu Thr Gln Val
145                 150                 155

<210> SEQ ID NO 6
<211> LENGTH: 105
<212> TYPE: PRT
<213> ORGANISM: Human papillomavirus

<400> SEQUENCE: 6

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
        50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 7
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 7

Asp Tyr Trp Lys His Met Arg Leu Glu Cys Ala Ile Tyr Tyr Lys Ala
1               5                   10                  15

Arg Glu Met Gly Phe Lys His Ile Asn His Gln Val Val Pro
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Arg Glu Met Gly Phe Lys His Ile Asn His Gln Val Val Pro Thr
1               5                   10                  15

Leu Ala Val Ser Lys Asn Lys Ala Leu Gln Ala Ile Glu Leu
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Arg Tyr Arg Phe Lys Lys His Cys Thr Leu Tyr Thr Ala Val Ser
1               5                   10                  15

Ser Thr Trp His Trp Thr Gly His Asn Val Lys His Lys Ser
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Ser Thr Trp His Trp Thr Gly His Asn Val Lys His Lys Ser Ala
1               5                   10                  15

Ile Val Thr Leu Thr Tyr Asp Ser Glu Trp Gln Arg Asp Gln
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
```

```
            20                  25                  30
```

<210> SEQ ID NO 12
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Leu Pro Gln Leu Cys Thr Glu Leu Gln Thr Thr Ile His Asp Ile Ile
1               5                   10                  15

Leu Glu Cys Val Tyr Cys Lys Gln Gln Leu Leu Arg Arg Glu Val Tyr
            20                  25                  30
```

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

```
Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25
```

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25
```

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25
```

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 16

His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25

<210> SEQ ID NO 17
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Tyr Gly Thr Thr Leu Glu Gln Gln Tyr Asn Lys Pro Leu Cys Asp
1               5                   10                  15

Leu Leu Ile Arg Cys Ile Asn Cys Gln Lys Pro Leu Cys Pro Glu Glu
            20                  25                  30

Lys

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

<210> SEQ ID NO 20
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
```

```
<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35

<210> SEQ ID NO 22
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 23
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35
```

INTRADERMAL HPV PEPTIDE VACCINATION

RELATED APPLICATIONS

The present invention is a U.S. National Phase filing of PCT/NL2008/050315, filed on May 27, 2008, which claims priority to European Patent Office application Number 07109287.8, filed on May 31, 2007 and claims the benefit of U.S. Application 60/941,070, filed on May 31, 2007, the entirety of which are herein incorporated by reference.

Sequence Listing

The instant appkicatsion contains a Sequence Listing which has been submitted via EFS-Web and is hereby incorporated by reference in its entirety. Said ASCII copy, created on Mar. 22, 2010, is named 85117306.txt and is 18,515 bytes in size.

FIELD OF THE INVENTION

The present invention relates to the field of medicine and immunology. In particular it relates to intradermal HPV peptide vaccination.

BACKGROUND OF THE INVENTION

HPV infection is highly prevalent among young, sexually active male and female individuals. Large prospective studies showed that acquisition of HPV from male partners is common, occurring in 40-60% of subjects during a 3 year follow-up period (Koutsky et al., 1997, Ho et al., 1998, Marrazzo et al., 2000). Therefore, HPV is probably the most common sexually transmitted disease.

Papillomaviruses of the high-risk types (e.g. HPV16, 18, 31, 33, and 45) are responsible for cervical cancer (Bosch et al., 1995, Zur Hausen, 1996). Following infection of the basal epithelial cells, the immediate HPV early genes E1, E2, E5, E6 and E7 are expressed. The E1 and E2 genes regulate viral replication. Furthermore, the E2 protein controls the expression of the E6 and E7 oncoproteins. The E6 protein of the high-risk HPV types specifically binds to p53 and targets its rapid degradation through the ubiquitin pathway. P53 is involved in initiation of apoptosis and loss of this protein result in the prevention of apoptosis (Scheffner et al., 1990). The E7 protein of high-risk types binds to pRB, which normally prevents cells from entering the cell cycle by inactivating E2F, a protein needed for cell cycle entry (Dyson et al. 1989). E7 expression results in the failure of infected cells to withdraw from the cell cycle and differentiate.

Prolonged and elevated expression of the E6 and E7 oncoproteins is tightly associated with HPV-induced dysplasia and transformation into cervical carcinoma.

The protective role of the immune system in the defense against HPV-related diseases and HPV-induced cancer in humans is suggested by the fact that compared to normal controls, immunosuppressed renal transplant patients and patients infected with HIV display a 17-fold greater incidence of genital HPV infection (Ho et al., 1994, Matorras et al. 1991, Halpert et al. 1986). The diminished capacity of immunosuppressed individuals to resolve HPV infection indirectly points towards a protective role of the immune system early in infection. Evidence of protection against HPV via immunity against the early antigens E2, E6 and E7 comes from the cottontail rabbit papillomavirus model which is the major animal model for cancer-associated papillomaviruses. Vaccination with the nonstructural proteins E1 and E2 induces the regression of virus-induced papillomas whereas viral tumor growth is suppressed.

Furthermore, rabbits vaccinated with the combination of the E1, E2, E6, and E7 genes were completely protected against viral challenge (Han et al. 1999, Selvakumar et al. 1995). Importantly, rabbits with progressively growing papilloma virus-induced warts could eradicate their lesions as well as clear latent viral infections following two injections with a vaccine comprising E6 and E7 long overlapping peptides (Vambutas, Vaccine 2005). These data indicate that immunity against E2, E6, and E7 can be effective as immunoprophylaxis of papillomavirus infection as well as therapeutically for HPV induced lesions and cancer.

Considerable interest exists in the identification of epitopes involved in the immune response to HPV16, given the possibility to incorporate these as subunits into a vaccine or to use these epitopes to monitor vaccine induced immunity in vivo. Since most epithelial cells express MHC class I but not class II, the attention has so far been focused on the induction of tumoricidal HPV-specific $CD8^+$ cytotoxic T lymphocytes (Melief et al., 2000; Ressing et al., 1995; Ressing et al., 2000; Ressing et al., 1996). HPV specific $CD8^+$ T-cell reactivity has been found in the peripheral blood of patients diagnosed with cervical intraepithelial neoplasia grade III (CIN III) lesions or cervical carcinoma (Nimako et al., 1997; Ressing et al., 1996) and in tumor-infiltrating T-cell populations isolated from patients with cervical cancer (Evans et al., 1997). Tumor specific $CD4^+$ T helper ("Th") immunity is now also considered pivotal for the efficient eradication of solid tumors, despite the fact that most of these tumors do not express MHC class II (reviewed in Melief et al., 2000; Pardoll and Topalian, 1998; Toes et al., 1999). Recent evidence indicates that $CD4^+$ tumor specific T-cells are required not only for optimal induction of $CD8^+$ tumor specific CTL but also for optimal exertion of local effector cell function by these CTL (Ossendorp et al., 1998, Toes et al., 1999). For induction of MHC class I restricted tumor-specific immunity, cross-presentation of antigens that have been captured by professional antigen presenting cells appears to play a dominant role. For proper induction of an effective tumor-specific CTL by cross-priming tumor-specific $CD4^+$ T cell help is required (Toes et al., 1999, Schoenberger et al., 1998).

Strong indications for a protective role of HPV-specific Th-immunity was suggested by the predomination of $CD4^+$ T-cells in regressing genital warts (Coleman et al., 1994) as well as by the detection of delayed-type hypersensitivity responses to HPV16 E7 in the majority of subjects with spontaneous regressing CIN lesions (Hopfl et al., 2000). Furthermore, in most healthy persons the immune system succeeds in eliminating the virus before malignancies develop (Koutsky, 1997; Evander, 1995). In line with this, more that half of all healthy females tested display strong proliferative HPV16 E2- and E6-specific Th1/Th2 cell memory responses (de Jong, 2002; Welters, 2003; de Jong, 2004). Furthermore, Th-reactivity against E2 was found to occur at time of viral clearance (Bontkes, 1999). Healthy subjects display HPV16 E7-specific immunity too (Welters, 2003; van der Burg, 2001). In contrast, the occurrence of HPV-induced cancer is strongly associated with immune failure. Analysis of HPV16 E2-, E6- and E7-specific $CD4^+$ T-cell immunity in the peripheral blood of patients with HPV16+ induced neoplasia revealed that half of the patients with high grade vulvar neoplasia (van Poelgeest, 2005) and the majority of patients with CIN III failed to mount a proper immune response (de Jong, 2004). Of the cervical carcinoma patients tested, approximately half lacked any detectable proliferative T-cell responses. The other half displayed weak proliferative HPV16 E2- and E6-specific T-cell responses not associated with the production of Th1/Th2 cytokines but with IL-10 (de Jong, 2004). This corroborates previous observations that E6- and E7-specific proliferative responses can be present (Luxton, 2003), but that the peripheral Th1 response in cervical carcinoma patients is low (de Gruijl, 1996; de Gruijl, 1998) or lacking (Tsukui, 1996). Because, the CD4+ T-cell response is of pivotal importance for the induction and maintenance of CD8+ CTL immunity (Melief, 2002), these data offer a plausible explanation why peripheral HPV16-specific CTL are rarely detected in patients with high-grade dysplasia or cancer (Ressing, 1996; Bontkes, 2000; Nimako, 1997; Youde, 2000), while such CTL are more commonly detectable in women without HPV16+ neoplasia (Nakagawa, 1997; Nakagawa, 1999).

For a clinically relevant approach of immunizing subjects against HPV in particular, it is preferred that both specific T-helper cells and CTL are induced. We have already shown that immunization with minimal CTL epitopes results in protection against tumors in some models (Kast et al. 1991) whereas, in other models, it can lead to tolerance or functional deletion of virus- and tumor-specific CTL that when otherwise induced are protective (Toes et al. 1996ab). The occurrence of tolerance or functional deletion decreases the effects of vaccination significantly. Epitopes involved with this effect were therefore not suitable for immunization purposes. Processing of exogenous antigens for presentation by MHC class 1 molecules by cross-priming as well as by other mechanisms is now widely recognized second pathway of processing for presentation by MHC class T, next to the well known endogenous route (Jondal et al. 1996, Reimann et al. 1997). The normal outcome of antigen processing via this pathway is CTL tolerance, unless APC activation by CD4+ T-cells takes place (Kurts et al., 1997). To solve this problem of tolerance or functional deletion, WO 02/070006 disclosed the use of long HPV peptides as a vaccine, said peptide having both a MHC Class I and II presentable epitopes resulting in the activation of both CD4+ and CD8+ T-cells.

HPV vaccines developed in WO 02/070006 may still further be improved since high doses of peptides and/or sequential vaccinations are usually used in order to get an optimal immunogenic effect. Furthermore, adjuvants such as Montanide ISA-51 are usually required to get an optimal immunogenic effect. These adjuvants induce undesired side-effects such as prolonged local swelling at the site of injection, red swollen hands, fever, vomiting, joint pain, a general illness feeling similar to symptoms experienced during influenza infection. These side effects are generally experienced as uncomfortable and will prevent treatment of patients with early stage lesions.

Therefore, there is still a need for improved HPV vaccines, which do not have all the drawbacks of the existing vaccines, among other, the HPV vaccine used in the invention does not necessitate high doses of peptides and/or sequential vaccinations and/or an adjuvant.

DESCRIPTION OF THE INVENTION

The invention relates to the use of a peptide derived from HPV-E2, -E6 and/or -E7 protein for the manufacture of a medicament for the treatment or prevention of an HPV related disease, wherein the medicament is for intradermal administration.

The sequence of the peptide used in the present invention is not critical as long as it is derived from an HPV-E2, -E6 and/or -E7 protein from HPV 16 or 18. Preferably, the peptide is chosen in one of the most immunogenic regions of these proteins. More preferably, the peptide is capable of inducing and/or enhancing an HPV-E2, -E6, and/or E7 specific T cell response, and therefore the peptide comprises a specific T cell epitope.

Peptides with a length that exceeds the length of HLA class I and class II epitopes (e.g. having a length as indicated herein) are particularly advantageous for use as a medicament because they are large enough to require the phagocytic machinery for antigen uptake as is present in professional antigen presenting cells (APC), in particular DC, as explained in WO02/070006 and processed in the DC before cell surface presentation of the contained HLA class I and class II epitopes takes place. Therefore, the disadvantageous induction of T cell tolerance (as shown in Toes et al., 1996, PNAS 93:7855 and Toes et al., 1996, J. Immunol. 156:3911), is prevented by the use of peptides having a length as indicated herein (as shown in Zwaveling et al., 2002, J. Immunol. 169:350). Therefore, in a preferred embodiment a use of the invention is provided wherein said peptide comprises a sequence capable of activating an APC. By a sequence capable of activating an APC is meant a sequence which is capable of at least partly activating an APC, preferably a professional APC. Said activation preferably leads to presentation of at least one epitope of said peptide at the surface of said APC. In a particularly preferred embodiment said peptide comprises at least two T cell epitopes for said antigen. The presence of two T cell epitopes for said antigen allows an even more efficient induction and/or enhancement of said antigen specific T cell response.

Preferably, at least one of said epitopes comprises a T-helper cell epitope for said antigen or a cytotoxic T lymphocyte (CTL) epitope for said antigen. Having at least one or the other epitope present on the peptide is favorable. Efficient induction and/or enhancement is achieved when said peptide comprises a T-helper activating sequence. By a T-helper activating sequence is meant herein a sequence capable of at least partly activating a T-helper cell. Said activation preferably leads to improved induction and/or enhancement of said antigen specific T cell response. In one embodiment said peptide comprises at least one T-helper cell epitope for said antigen and at least one cytotoxic T lymphocyte (CTL) epitope for said antigen.

Accordingly, a peptide is preferably used, wherein at least one HLA class II (T helper cell) epitope and/or at least one HLA class T (cytotoxic T cell) epitope are present within a contiguous amino acid sequence from the amino acid of the HPV E2 or E6 and/or E7 protein from a high risk HPV serotype such as serotype 16, 18, 31, 33, or 45. More preferably, the contiguous amino acid sequence present in a peptide used are from the amino acid of the HPV E2, E6 or E7 protein from HPV serotype 16, 18, 31, or 33, even more preferably from HPV serotype 16 or 18 and most preferably from HPV serotype HPV 16. The amino acid sequences of HPV16 and HPV18 E2, E6 and E7 are depicted in SEQ ID No.1, 2, 3, 4, 5 and 6 respectively.

Preferably the length of the contiguous amino acid sequence is no more than 45 amino acids and comprises at least 19 amino acids selected from the amino acid sequence of the HPV16 or HPV18 E2, E6 and/or E7 protein (e.g. SEQ ID No. 1, 2, 3, 4, 5, 6), wherein the peptide comprises at least one HLA class II epitope and/or at least one HLA class I epitope, both from the amino acid sequence of the HPV E2, E6 and/or E7 protein. More preferably, in the peptide at least one HLA class II epitope and/or at least one HLA class I epitope are present within a contiguous amino sequence from the amino acid sequence of the HPV E2, E6 and/or E7 protein.

For sake of clarity the peptide used in the invention preferably comprises at least one HLA class I epitope and/or at least one HLA class II epitope, each of these epitopes are presentable and will bind to the corresponding specific HLA molecule present on the cells after having been processed as described herein. Each HLA epitope may therefore also be named a HLA binding and/or presentable epitope. More preferably, the peptide used is capable of inducing and/or enhancing an HPV-E2, -E6, and/or E7 specific T cell response, wherein the peptide comprises a T cell epitope specific for said HPV-E2, -E6, and/or E7 protein. Even more preferably, the peptide comprises 22-45 contiguous amino acid residues from the HPV E2, or E6 and/or E7 protein.

The length of the contiguous amino acid sequence from the HPV E2, E6 and/or E7 protein comprised within the peptide, preferably is comprised between 19-45, 22-45, 22-40, 22-35, 24-43, 26-41, 28-39, 30-40, 30-37, 30-35, 32-35 33-35, 31-34 amino acids. In another preferred embodiment, the peptides comprises 22, 23, 24, 25, 26, 27, 28, 29, 30, 31, 32, 33, 34, 35, 36, 37, 38, 39, 40, 41, 42, 43, 44, or 45 or more than 45 contiguous amino acid residues of the HPV E2, E6 and/or E7 protein. In another preferred embodiment, the peptide of the invention consists of any of the contiguous amino acid sequences from the HPV E2, E6 and/or E7 protein as defined herein. The peptides used in the invention may be easily synthesized and are large enough to be taken up by professional APCs, processed by the proteasome and have sufficient physical capacity and length to contain at least one HLA class I and/or one HLA class II epitope. Accordingly as defined above, in a preferred embodiment, the peptide comprises a sequence capable of activating an APC.

Alternatively or in combination with former preferred embodiment, the peptide comprises a T helper activating sequence.

In an even more preferred embodiment, the peptide comprises at least two T cell epitopes for said antigen. Most preferably, in this peptide at least one of said epitopes comprises a T-helper cell epitope for said antigen and/or a cytotoxic T lymphocyte (CTL) epitope for said antigen.

In another preferred embodiment, the antigen present in the peptide derives from the HPV E2, E6 and/or E7 protein or an immunogenic part, derivative and/or analogue thereof. An immunogenic part, derivative and/or analogue of a protein comprises the same immunogenic capacity in kind not necessarily in amount as said protein itself. A derivative of such a protein can be obtained by preferably conservative amino acid substitution.

More preferably, said peptide comprises E2, E6 and/or E7 regions that were identified herein as most immunogenic ones. Furthermore, a number of naturally processed Th-epitopes mapping in this region has already been identified. Methods included respectively short and long-term PBMC cultures derived from healthy blood donors may be used to identify suitable peptides. The PBMC cultures may be stimulated with the peptides to be tested. In parallel, the in vivo induced E2, E6 and/or E7-specific immunity, as detected by IF/γ ELISPOT assays, may be analyzed in healthy subjects as well as subjects diagnosed with HPV16+ lesions.

In a preferred embodiment, the medicament used herein comprises at least two different peptides derived from the HPV-E2, E6 and/or E7 proteins. More preferably, at least three, at least four, at least five, at least six, at least seven, at least eight or more peptides are used in combination as a mix or a pool in the medicament. This is advantageous since vaccination and subsequent protection could be obtained for several immunogenic epitopes present within one HPV protein E2, E6 or E7 using one single type of vaccine.

Alternatively or in combination with former preferred embodiment, the medicament comprises peptides whose contiguous amino acid sequences are derived from at least two of the HPV E2, E6 and E7 proteins, more preferably from all three of the HPV E2, E6 and E7 proteins. This is also advantageous since vaccination and subsequent protection could be obtained for several immunogenic epitopes present within several HPV proteins E2, E6 or E7 using one single type of vaccine.

When the medicament used comprises more than one peptide, the combination of several peptides may also be named pool or mix of peptides.

In a preferred embodiment, the medicament comprises at least one of the following peptides, each peptide comprises or consists of or overlaps with the following sequences derived from E2, E6 or E7 of HPV16: E2 31-60 or SEQ ID NO:7, E2 46-75 or SEQ ID NO:8, E2 301-330 or SEQ ID NO:9, E2 316-345 or SEQ ID NO:10, E6 1-32 or SEQ ID NO:11, E6 19-50 or SEQ ID NO:12, E6 41-65 or SEQ ID NO:13, E6 55-80 or SEQ ID NO:14, E6 71-95 or SEQ ID NO:15, E6 85-109 or SEQ ID NO:16, E6 91-122 or SEQ ID NO:17, E6 109-140 or SEQ ID NO:18, E6 127-158 or SEQ ID NO:19, E7 1-35 or SEQ ID NO:20, E7 22-56 or SEQ ID NO:21, E7 43-77 or SEQ ID NO:22, E7 64-98 or SEQ ID NO:23, E2 1-30, E2 16-45, E2 61-90, E2 51-70, E2 61-76, E2 76-105, E2 91-120, E2 106-135, E2 121-150, E2 136-165, E2 151-180, E2 166-195, E2 181-210, E2 196-225 E2 211-240, E2 226-255, E2 241-270, E2 256-285, E2 271-300, E2 286-315, E2 316-330, E2 311-325, E2 331-365, E2 346-355, E2 351-365, E6 1-22, E6 11-32, E6 21-42, E6 31-52, E6 41-62, E6 51-72, E6 61-82, E6 71-92, E6 81-102, E6 91-112, E6 101-122, E6 111-132, E6 121-142, E6 127-140, E6 131-152, E6 137-158, E7 1-22, E7 11-32, E7 21-42, E7 30-50, E7 31-52, E7 35-50, E7 41-62, E7 50-62, E7 51-72, E7 35-77, E7 61-82, E7 71-92, E7 77-98, of which E2 31-60 or SEQ ID NO:7, E2 46-75 or SEQ ID NO:8, E2 301-330 or SEQ ID NO:9, E2 316-345 or SEQ ID NO:10, E6 1-32 or SEQ ID NO:11, E6 19-50 or SEQ ID NO:12, E6 41-65 or SEQ ID NO:13, E6 55-80 or SEQ ID NO:14, E6 71-95 or SEQ ID NO:15, E6 85-109 or SEQ ID NO:16, E6 91-122 or SEQ ID NO:17, E6 109-140 or SEQ ID NO:18, E6 127-158 or SEQ ID NO:19, E7 1-35 or SEQ ID NO:20, E7 22-56 or SEQ ID NO:21, E7 43-77 or SEQ ID NO:22, E7 64-98 or SEQ ID NO:23 are most preferred. The sequence of each of these peptides can be deduced from the full length sequence of the corresponding E2, E6 or E7 of HPV16 as depicted in SEQ ID NO: 1, 2, or 3.

In the context of the invention, overlapping means that the sequence of the peptide used partially or totally overlaps with the given sequence. Preferably, overlapping means partially overlapping. Partially preferably means that the overlap is of one or more amino acids at the 5' end and/or at the 3' end of the peptide sequence, more preferably of two or more amino acids at the 5' end and/or at the 3' end, or more. It is also preferred that the overlap is of one or more amino acids at the 5'end and/or two or more amino acids at the 3' end of the peptide sequence or vice versa. The skilled person will understand that all kinds of overlaps are encompassed by the present invention as long as the obtained peptide exhibits a desired immunogenic activity as earlier defined herein.

In another preferred embodiment, the peptides used in the medicament are derived from the sequences given above by conservative amino acid substitution.

More preferably, the medicament comprises at least two of the peptides as specifically mentioned above are used, or at least three or at least four, or at least five, or at least six or more.

In most preferred embodiments, the medicament comprises at least one of the following pools of peptides, wherein each peptide comprises or consists of or overlaps with the following sequences:
pool 1: E2 31-60 and/or E2 46-75, and/or
pool 2: E2 301-330 and/or E2 316-345, and/or
pool 3: E2 31-60 and/or E2 46-75, and/or E2 301-330 and/or E2 316-345, and/or
pool 4: E6 1-32 and/or E6 19-50, and/or
pool 5: E6 41-65, E6 55-80 and/or E6 71-95, and/or
pool 6: E6 85-109, and/or E6 91-122 and/or
pool 7: E6 109-140 and/or E6 127-158, and/or
pool 8: E6 1-32 and/or E6 19-50, and/or E6 41-65, and/or E6 55-80 and/or E6 71-95, and/or E6 85-109, and/or E6 91-122 and/or E6 109-140 and/or E6 127-158, and/or
pool 9: E7 1-35 and/or E7 22-56, and/or
pool 10: E7 43-77, and/or E7 64-98, and/or
pool 11: E7 1-35 and/or E7 22-56, and/or E7 43-77, and/or E7 64-98, and/or
pool 12: pool 3 and pool 8 as defined above, and/or
pool 13: pool 8 and pool 11 as defined above, and/or
pool 14: pool 3 and pool 11 as defined above, and/or
pool 15: pool 3, pool 8 and pool 11 as defined above.

Preferably, the class II CD4+ Th cell epitope comprised in a peptide present in the medicament is capable of activating a CD4+ Th cell in the patient with HPV-induced disease and/or a healthy subject. The activation is preferably assessed ex vivo or in vivo, more preferably in the patient with HPV-induced disease of whom the HPV-infected/transformed cells express the given antigen. Most preferably, the HLA class II epitope is capable of activating a CD4+ Th memory response, i.e. activation of a CD45 RO-positive CD4+ T-helper cell. This will lead, by virtue of the 'licence to kill' signal through CD40-triggering of DC (Lanzavecchia, 1998, Nature 393:413), to a more robust CD8+ effector and memory T-cell response.

The art currently knows many ways of generating a peptide. The invention is not limited to any form of generated peptide as long as the generated peptide comprises a minimal T cell epitope. By way of example, a peptide present in the medicament can be obtained from protein E2, E6 or E7, synthesized in vitro or by a cell, for instance through an encoding nucleic acid. A peptide used in the medicament can be present as a single peptide or incorporated into a fusion protein. In one embodiment said peptide is flanked by processing sites allowing processing of said peptide inside a cell such as to allow transport and/or incorporation into an MHC molecule on the surface of said cell. In a preferred embodiment a peptide used in the medicament is after processing capable of complexing with an MHC class II molecule. MHC class II restricted T-cell immunity is currently considered to be important in eradication of for instance tumor cells although said tumor cells often do not express MHC class II molecules. Peptides used in the medicament are particularly well suited for eliciting, inducing and/or stimulating both MHC class I and MHC class II dependent T cells.

A peptide used in the medicament may further be modified by deletion or substitution of one or more amino acids, by extension at the N- and/or C-terminus with additional amino acids or functional groups, which may improve bio-availability, targeting and uptake by professional APC, or comprise or release immune modulating substances that provide adjuvant or (co)stimulatory functions. The optional additional amino acids at the N- and/or C-terminus are preferably not present in the corresponding positions in the HPV E2, E6 and/or E7 amino acid sequence, more preferably they are not from the E2, E6, or E7 amino acid sequence (SEQ ID NO. 1, 2, 3, 4, 5, 6).

In a further preferred embodiment, the medicament does not comprise an adjuvant. More preferably, the medicament does not comprise an adjuvant currently known to be associated with at least one of the following undesired side effects such as local swelling at the site of injection, red swollen hands, fever, vomiting, joint pain, a general illness feeling similar to symptoms experienced during an infection with influenza. Even more preferably, the adjuvant is not of the type of an oil-in water emulsions such as incomplete Freund's adjuvant or IFA, Montanide ISA-51 or Montanide ISA 720 (Seppic France). Even more preferably, the adjuvant does not have a depot function and/or is biological degradable. A depot function preferably means that the peptide is contained for a long time in the injection site and only leaks out over a long time period. Preferably, a long time period is of at least one month, more preferably at least two, or three months. Even more preferably, the adjuvant is not Montanide ISA-51 (Seppic France).

In another further preferred embodiment, the medicament consists of one or more peptides as earlier defined herein and an inert pharmaceutically acceptable carrier and/or excipients. The inert pharmaceutically acceptable carrier and/or excipients preferably is inert in the sense that it does not invoke an immune response and/or an inflammatory response or any of the undesired side effects described above for adjuvants. Formulation of medicaments, and the use of pharmaceutically acceptable excipients are known and customary in the art and for instance described in Remington; The Science and Practice of Pharmacy, $21^{nd}$ Edition 2005, University of Sciences in Philadelphia. The medicament used in the invention is formulated to be suitable for intradermal administration or application. Intradermal is known to the skilled person. In the context of the invention, intradermal is synonymous with intracutaneous and is distinct from subcutaneous. A most superficial application of a substance is epicutaenous (on the skin), then would come an intradermal application (in or into the skin), then a subcutaneous application (in the tissues just under the skin), then an intramuscular application (into the body of the muscle). An intradermal application is usually given by injection. An intradermal injection of a substance is usually done to test a possible reaction, allergy and/or cellular immunity to it. A subcutaneous application is usually also given by injection: a needle is injected in the tissues under the skin.

In another further preferred embodiment, since the medicament used in the invention does not comprise any adjuvant such as Montanide ISA-51, it means the formulation of the medicament is more simple: an oil-water based emulsion is preferably not present in the medicament used. Accordingly, the medicament used in the invention does not comprise an adjuvant such as Montanide ISA-51 and/or does not comprise an oil-in-water based emulsion. Therefore, in a preferred embodiment, the medicament used in the invention is a buffered aqueous solutions at physiological ionic strength and/or osmolarity, such as e.g. PBS (Phosphate Buffer Saline) comprising or consisting of one or more peptide as defined earlier herein. The skilled person knows how to prepare such a solution.

The medicament as used in the invention has another advantage, which is that by intradermally administering low amounts of a peptide as earlier herein defined, an immunogenic effect may still be achieved. The amount of each peptide used is preferably ranged between 1 and 1000 μg, more preferably between 5 and 500 μg, even more preferably between 10 and 100 μg.

The skilled person would know how to test whether the concentration of peptide envisaged is immunogenic. Preferably, PBMC are in vitro stimulated with different concentrations of a peptide to be tested as illustrated in WO 02/070006. In example, an immunogenic effect is reached when peptide-stimulated PBMC start to proliferate at least 2 times stronger, and/or produce at least 2-fold more cytokine, and/or upregulate activation markers (e.g. CD25, HLA-DR, CD69, CD154, CD137) than non-stimulated PBMC. Alternatively, a skin test is performed as in the examples. Briefly, the chosen peptide is intracutaneously injected, preferably 0.05 ml of about 0.1 to about 0.4 mg/ml, more preferably 0.2 mg/ml peptides in about 10-20%, more preferably about 16% DMSO (v/v) in 20 mM isotonic phosphate buffer (10 μg/peptide). The peptides are injected separately at individual skin test sites of the upper arm.

In another preferred embodiment, the medicament comprises a peptide as earlier defined herein and at least one adjuvant, said adjuvant being not formulated in an oil-in water based emulsion and/or not being of an oil-in-water emulsion type as earlier defined herein. This type of medicament may be administered as a single administration. Alternatively, the administration of a peptide as earlier herein defined and/or an adjuvant may be repeated if needed and/or distinct peptides and/or distinct adjuvants may be sequentially administered. It is further encompassed by the present invention that a peptide of the invention is administered intradermally whereas an adjuvant as defined herein is sequentially administered. The adjuvant may be intradermally administered. However any other way of administration may be used for the adjuvant.

Particularly preferred adjuvants are those that are known to act via the Toll-like receptors and/or via a RIG-1 (Retinoic acid-inducible gene 1) protein and/or via an endothelin receptor. Adjuvants that are capable of activation of the innate immune system, can be activated particularly well via Toll like receptors (TLR's), including TLR's 1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heatshock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *Streptococcus* heat labile soluble factor (GBS-F) or *Staphylococcus* modulins. TLR7 may be activated by imidazoquinolines. TLR9 may be activated by unmethylated CpG DNA or chromatin—IgG complexes. In particular TLR3, TLR7 and TLR9 play an important role in mediating an innate immune response against viral infections, and compounds capable of activating these receptors are particularly preferred for use in the invention. Particularly preferred adjuvants comprise, but are not limited to, synthetically produced compounds comprising dsRNA, poly(I:C), unmethylated CpG DNA which trigger TLR3 and TLR9 receptors, IC31, a TLR 9 agonist, IMSAVAC, a TLR 4 agonist. RIG-1 is known to be activated by ds-RNA just like TLR3 (Immunity (2005), 1:19-28). In another preferred embodiment, the adjuvants are physically linked to a peptide as earlied defined herein. Physical linkage of adjuvants and costimulatory compounds or functional groups, to the HLA class I and HLA class II epitope comprising peptides provides an enhanced immune response by simultaneous stimulation of antigen presenting cells, in particular dendritic cells, that internalize, metabolize and display antigen. Another preferred immune modifying compound is a T cell adhesion inhibitor, more preferably an inhibitor of an endothelin receptor such as BQ-788 (Buckanovich R J et al Ishikawa K, PNAS (1994) 91:4892). BQ-788 is N-cis-2,6-dimethylpiperidinocarbonyl-L-gamma-methylleucyl-D-1-methoxycarbonyltryptophanyl-D-norleucine. However any derivative of BQ-788 or modified BQ-788 compound is also encompassed within the scope of this invention.

Furthermore, the use of APC (co)stimulatory molecules, as set out in WO99/61065 and in WO03/084999, in combination with a peptide present in the medicament used in the invention is preferred. In particular the use of 4-1-BB and/or CD40 ligands, agonistic antibodies, OX40 ligands or functional fragments and derivates thereof, as well as synthetic compounds with similar agonistic activity are preferably administered separately or combined with a peptide present in the medicament to subjects to be treated in order to further stimulate the mounting an optimal immune response in the subject.

In a preferred embodiment, the adjuvant comprises a TLR (3,4,7,8,9) ligand such as monophosphoryl lipid A and/or CpG nucleic acid, and/or an APC-costimulatory molecule such as a CD40 ligand, agonistic antibodies or functional fragments and derivates thereof, and/or GM-CSF.

In another preferred embodiment, to promote the presentation of a peptide by a professional antigen presenting cell or dendritic cells, the medicament comprising a peptide further comprises a DC-activating agent as a TLR ligand as earlier mentioned herein.

In a preferred embodiment, the medicament, which is a vaccine is administered to a human or animal. In a more preferred embodiment, the human or animal is suffering from or at risk of suffering from a HPV (persistent) related disease. Said HPV related disease is selected from an HPV infection, an HPV associated malignancy, a Cervical Intra-epithelial Neoplasia (CIN), a Vulva Intra-epithelial Neoplasia (VIN), an Anal Intra-epithelial Neoplasia (AIN), a Vaginal Intra-epithelial Neoplasia (VAIN), Penile Intra-epithelial Neoplasia (PIN), cervical cancer, head and neck cancer, in particular oropharyngeal cancer and tonsillar cancers, penile cancer, anal cancer, vaginal cancer and vulvar cancer.

Preferably, said HPV related disease is at least in part treatable or preventable by inducing and/or enhancing said immune response.

The method of the invention is therefore very suited for providing a subject with immunity against said antigen and/or for enhancing said immunity. Methods of the invention are suitable for any purpose that other immunization strategies are used for. Old immunizations are used for vaccination purposes, i.e. for the prevention of disease. However, methods of the invention are not only suitable for preventing disease. Methods can also be used to treat existing disease, of course with the limitations that the disease is treatable by inducing and/or enhancing antigen specific T cell immunity. This feature can be used to treat, for instance, diseases associated with viral infections such as HPV infection, such as some cancers. In a preferred embodiment said human or animal is suffering from or at risk of suffering from a disease such as an HPV infection that is at least in part treatable or preventable by inducing and/or enhancing said immune response. Preferably said disease comprises a HPV viral disease and/or cancer.

The intradermal administration of a peptide is very attractive since the injection of the vaccine is realized at or as close by as possible to the site of the disease resulting in the local activation of the disease draining lymph node, resulting in a stronger local activation of the immune system. In particular for VIN, VAIN, AIN, PIN, Penile cancer, Vulva cancer, Anal cancer, Head and Neck cancers.

In a preferred embodiment, the intradermal administration is carried out directly at the site of the lesion or disease. At the site of the lesion is herein understood to be within less than 5, 2, 1, 0.5, 0.2 or 0.1 cm from the site of the lesion.

Upon intradermally administering a medicament as defined herein, not only Th2 but also Th1 responses are triggered. This is surprising since it was already found that cutaneous antigen priming via gene gun lead to a selective Th2 immune response (Alvarez D, et al, 2005). Furthermore, the immune response observed is not only restricted to the skin as could be expected based on Alvarez D., et al. We demonstrate that specific T cells secreting IFNγ circulate through the secondary lymph system as they are detected in the post challenged peripheral blood.

Another crucial advantage of the medicament of the invention is that relatively low amounts of peptides may be used, in one single shot, in a simple formulation and without any adjuvant known to give undesired side-effects as Montanide ISA-51. Without wishing to be bound by any theory, we believe the HPV intradermal peptide(s) used in the invention specifically and directly targets the epidermal Langerhans cells (LC) present in the epithelium. Langerhans cells are a specific subtype of DC which exhibit outstanding capacity to initiate primary immune responses (Romani N., et al,). These LC may be seen as natural adjuvants recruited by the medicament used in the invention.

In another preferred embodiment, the invention relates to the use of a peptide derived from HPV-E2, -E6 and/or -E7 protein for the manufacture of a medicament for the treatment or prevention of an HPV related disease, wherein the medicament is for intradermal administration as earlier defined and wherein in addition a peptide derived from HPV-E2, -E6 and/or -E7 protein is further used for the manufacture of a medicament for the treatment or prevention of an HPV related disease, wherein the medicament is for subcutaneous administration.

The medicament for intradermal administration has already been defined herein. The peptide used for subcutaneous administration is the same as the one used for intradermal administration and has already been defined herein. The skilled person knows how to formulate a medicament suited for subcutaneous administration. Preferably, the medicament suited for subcutaneous administration comprises a peptide as already herein defined in combination with an adjuvant. Preferred adjuvants have already been mentioned herein. Other preferred adjuvants are of the type of an oil-in water emulsions such as incomplete Freund's adjuvant or IFA, Montanide ISA-51 or Montanide ISA 720 (Seppic France). In a further preferred embodiment, the medicament suited for subcutaneous administration comprises one or more peptides, an adjuvant both as earlier defined herein and an inert pharmaceutically acceptable carrier and/or excipients all as earlier defined herein. Formulation of medicaments, and the use of pharmaceutically acceptable excipients are known and customary in the art and for instance described in Remington; The Science and Practice of Pharmacy, $21^{nd}$ Edition 2005, University of Sciences in Philadelphia. The second medicament used in the invention is formulated to be suitable for subcutaenous administration.

In this preferred embodiment, the medicament suited for intradermal administration may be simultaneously administered with the medicament suited for subcutaneous administration. Alternatively, both medicament may be sequentially intradermally and subsequently subcutaneously administered or vice versa (first subcutaneous administration followed by intradermal administration). In this preferred embodiment as in earlier preferred embodiment dedicated to the intradermal administration, the intradermal and/or subcutaneous administration of a peptide as earlier herein defined and/or of an adjuvant may be repeated if needed and/or of distinct peptides and/or of distinct adjuvants may be sequentially intradermally and/or subcutaneously administered. It is further encompassed by the present invention that a peptide of the invention is administered intradermally and/or subcutaneously whereas an adjuvant as defined herein is sequentially administered. The adjuvant may be intradermally and/or subcutaneously administered. However any other way of administration may be used for the adjuvant.

We expect the combination of an intradermal and a subcutaneous administration of a medicament according to the invention is advantageous. DC in the epidermis are clearly different from DC in the dermis and in the subcutis. The intracutaneous (intradermal) immunization will cause antigen processing and activation of epidermal DC (Langerin-positive langerhans cells) that through their dendritic network are in close contact with the keratinocytes. This will also optimally activate inflammatory pathways in the interactions between Langerhans cell and keratinocytes, followed by trafficking of antigen loaded and activated Langerhans cell to the skin-draining lymph nodes.

The subcutaneous administration will activate other DC subsets, that will also become loaded with antigen and travel independently to the skin-draining lymph nodes. Conceivably, the use of a medicament which may be administered both intradermally and subcutaneously may lead to a synergistic stimulation of T-cells in these draining nodes by the different DC subsets.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The invention is further illustrated by the following examples, which should not be construed for limiting the scope of the invention.

Figure 1:
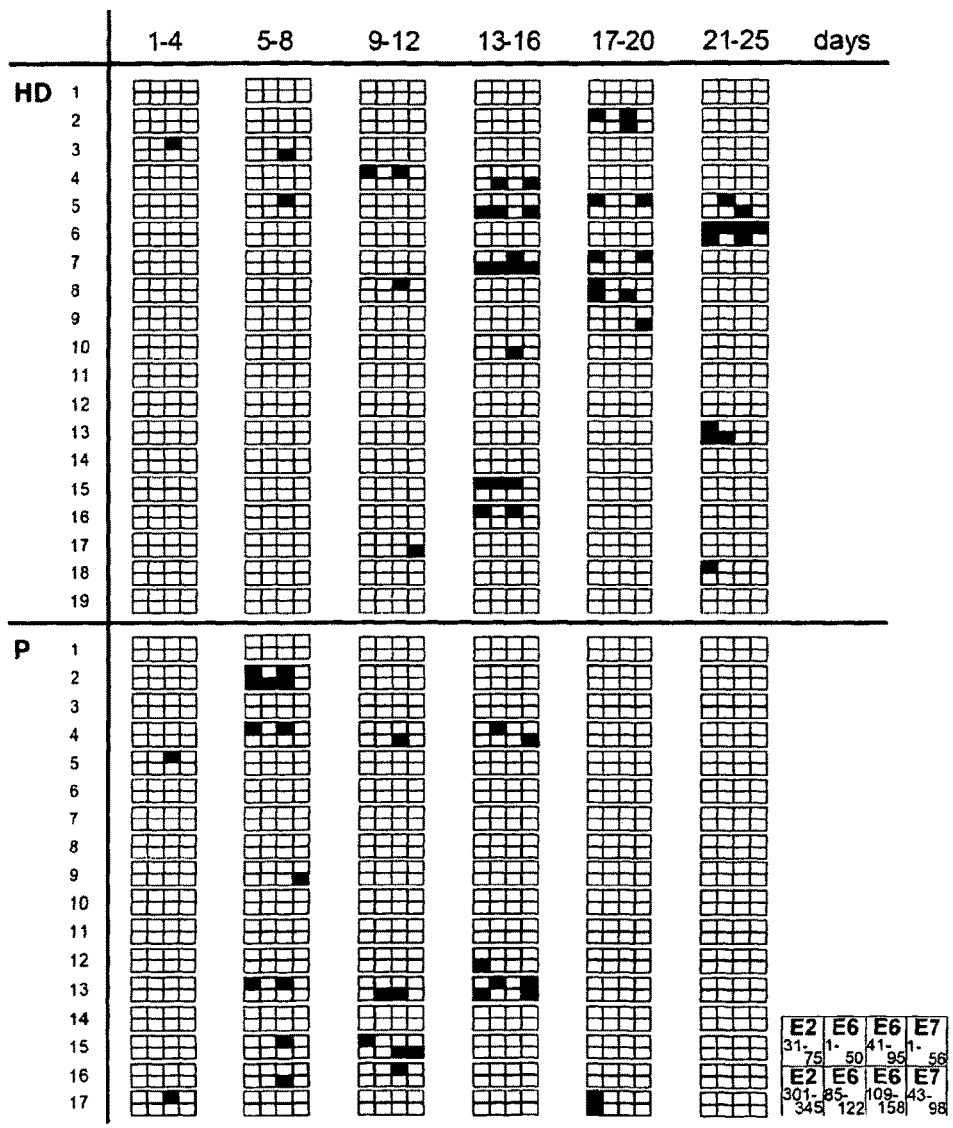
FIG. 1

An overview of the number, day of appearance and injected antigen that induced a positive skin reactions in the group of 19 healthy donors (HD) and 17 patients (P) with history of cervical neoplasia. Skin reactions were considered positive when papules greater then 2 mm in diameter arose no less then 2 days after injection. The indicated layout is used for the 8 peptide pools, the first and last amino acid in the protein of the peptide pool used is indicated. The layout printed in bold indicates at least one positive reaction within this timeframe; a filled square represents a new developed, positive skin reaction to the indicated peptide pool.

FIG. 2

Detection of HPV16 specific T cells by IFNγ ELIspot in the pre-challenge blood sample of healthy donors is significantly correlated with the appearance of an early (<13 days) positive skin reaction to the recognized peptide pool (p=0.0003, two tailed Fisher's Extract test). Specific responses were calculated by subtracting the mean number of spots+2×SD of the medium control from the mean number of spots in experimental wells. The number of specific spots per 100.000 PBMC is given. Responses were considered positive if peptide pool specific T cell frequencies were ≥5 in 100.000 PBMCs.

FIG. 3

A. Association between the appearance of a positive skin reaction and the simultaneous detection (IFNγ ELIspot) of circulating HPV16 specific T cells in the post-challenge blood sample of healthy donors (p<0.0001, two tailed Fisher's exact test). From a total of 88 skin tests, 39 were positive. Twenty-five of these 39 reactions were associated with a positive reaction in ELIspot (T cell frequency≥5 in 100.000 PBMCs). Of the 49 skin test sites that did not show a skin reaction, 10 were associated with a positive ELIspot.

B. Example of a healthy donor (HD10) displaying a positive skin reaction at day 14 to peptide pool 6 ($E6_{109-140}$, $E6_{127-158}$) (left panel). Punch biopsy of the positive skin reaction site (right panel).

FIG. 4

A. HPV16 specific T cell responses detected by IFNγ ELIspot in the post-challenge blood sample of healthy donors displaying a positive skin reaction. The mean number of spots per 100.000 PBMCs are depicted. Memory response mix (MRM) was used as a positive control. The filled bar indicates the positive skin reaction site of which a punch biopsy was taken and put in to culture.

B. T lymphocytes exfiltrating from punch biopsies were, after a 14- to 28 day period of cytokine driven expansion, tested for their capacity to proliferate upon stimulation with monocytes pulsed with peptides (10 μg/ml)—as injected in the skin test—or with protein (20 μg/ml). Phytohemagglutinine (PHA) served as a positive control. Proliferation was measured by [$^3$H]thymidine incorporation and a proliferative response was defined specific as the stimulation index (SI)≥3. Healthy donor 17 (HD17) is an example of a positive skin reaction site consisting of non specific T cells.

C. Supernatants of the proliferative responses in B were analysed for the presence of IFNγ, interleukin 4 (IL4), IL5 and tumor necrosis factor α, IL2, IL10 (not shown) by cytometric bead array. Cutoff values were based on the standard curves of the different cytokines (100 μg/ml IFNγ and 20 pg/ml for the remaining cytokines). Antigen-specific cytokine production was defined as a cytokine concentration above cutoff level and >2× the concentration of the medium control. Healthy donor 15 (HD15) displays a high background level of IL5, but is increased >2× after antigen stimulation.

FIG. 5.

T cell culture of the skin biopsy of pool 4 ($E6_{41-65}$, $E6_{55-80}$, $E6_{71-95}$) of healthy donor 15 (HD15) consists of both HPV16 specific CD4+ and CD8+ T cells. The specificity of the culture was tested in an intracellular cytokine staining (ICS) against the protein (20 μg/ml) and the peptides (10 μg/ml) corresponding with the injected skin test. Remarkably, in 3 out of 4 biopsies CD8+ HPV 16-specific T cells were detected.

EXAMPLES

Materials and Methods

Study Design

A cross-sectional pilot study to analyse HPV16 E2-, E6-, and E7-specific T-cell responses as measured by intradermal injection of pools of clinical grade HPV16 peptides in the upper arm was performed in patients with HPV-related disorders of the cervix and in healthy individuals. Since a delayed type hypersensitivity reaction represents a memory T-cell response, there was no prerequisite for HPV16-positivity at the time of analysis.

Subjects

Seventeen women (P) with history of cervical carcinoma (n=12) or CIN (n=5) and a group of nineteen healthy individuals (HD) participated in this study after providing informed consent. The clinical characteristics of the patients, including HPV status, are summarized in Table 1. The age of the patients ranged from 28-72 years (median age, 46 years). The group of healthy individuals displayed a median age of 31 years old (range, 20-51 years) and was comprised of 80% women and 20% males. Peripheral blood mononuclear cells (PBMCs) were obtained from all subjects immediately before administration of the skin test. The late appearance of positive skin tests in healthy individuals resulted in the isolation of a second blood sample from 11 of 19 healthy volunteers. The study design was approved by the Medical Ethical Committee of the Leiden University Medical Centre.

DTH Skin Test

Skin tests, based on Delayed Type Hypersensitivity reactions (DTH), can be used as a sensitive and simple method for in vivo measurement of HPV-specific cellular immune responses (Hopfl, 2000; Hopfl, 1991). The skin test preparations consisted of 8 pools of long clinical-grade synthetic peptides spanning the whole HPV 16 E6 and E7 protein and the most immunogenic regions of HPV 16 E2 protein (de Jong, 2004). These clinical grade peptides were produced in the interdivisional GMP-Facility of the LUMC. Each pool of the skin test consisted of 2 or 3 synthetic peptides, indicated by the first and last amino acid of the region in the protein covered by the peptides. Pool 1: $E2_{31-60}$, $E2_{46-75}$, Pool 2: $E2_{301-330}$, $E2_{316-345}$, Pool 3: $E6_{1-31}$, $E6_{19-50}$, Pool 4: $E6_{41-65}$, $E6_{55-80}$, $E6_{71-95}$, Pool 5: $E6_{85-109}$, $E6_{91-122}$, Pool 6: $E6_{109-140}$, $E6_{127-158}$, Pool 7: $E7_{1-35}$, $E7_{22-56}$, Pool 8: $E7_{43-77}$, $E7_{64-98}$. Per peptide pool 0.05 ml of 0.2 mg/ml peptides in 16% DMSO in 20 mM isotonic phosphate buffer (10 μg/peptide) was injected intracutaneously. The pools of peptides and a negative control (dissolvent only) were injected separately at individual skin test sites of the upper arm. Skin test sites were inspected at least three times, at 72 hours and 7 days after injection (Hopfl) of the peptides and at 3 weeks following the first report of a very late skin reaction in one of the first healthy subjects. Reactions were considered positive when papules greater than 2 mm in diameter arose no less than 2 days after injection. From positive skin reaction sites punch biopsies (4 mm) were obtained, cut in small pieces and cultured in IMDM containing 10% human AB serum, 10% TCGF and 5 ng/ml IL7 and IL15 to allow the emigration of lymphocytes out of the skin tissue. After 2 to 4 weeks of culture the expanded T cells were harvested and tested for their HPV-specific reactivity.

Antigen for In Vitro Immune Assays

A set of peptides, similar to the peptides used in the skin test, were used for T—cell stimulation assays and IFNγ-ELISPOT assays. The four HPV 16 E2 peptides consisted of 30-mer peptides overlapping 15 residues, HPV 16 E6 consisted of 32-mers and HPV 16 E7 of 35-mers, both overlapping 14 residues. The peptides were synthesized and dissolved as previously described (van der Burg, 1999). Notably, in the IFNγ ELISPOT assays peptide pool 4 and 5 slightly differed from the peptide pools used in the skin test, pool 4 contained peptides $E6_{37-68}$, $E6_{55-86}$, $E6_{73-104}$ and pool 5 comprised peptides $E^6_{73-104}$, $E6_{91-122}$.

Memory response mix (MRM 50×), consisting of a mixture of tetanus toxoid (0.75 Limus flocculentius/ml; National Institute of Public Health and Environment, Bilthoven, The Netherlands), Mycobacterium tuberculosis sonicate (5 µg/ml; generously donated by Dr. P. Klatser, Royal Tropical Institute, Amsterdam, The Netherlands), and Candida albicans (0.15 mg/ml, HAL Allergenen Lab., Haarlem, The Netherlands) was used as a positive control. Recombinant HPV 16 E2, E6 and E7 proteins were produced in recombinant Escherichia coli as described previously (van der Burg, 2001).

Analysis of Antigen-Specific Th Cells by IFNγ ELISPOT

The presence of HPV 16-specific Th Cells was analyzed by ELISPOT as described previously (van der Burg, 2001) Briefly, fresh PBMCs were seeded at a density of $2 \times 10^6$ cells/well of a 24-well plate (Costar, Cambridge, Mass.) in 1 ml of IMDM (Bio Whittaker, Verviers, Belgium) enriched with 10% human AB serum, in the presence or absence of the indicated HPV 16 E2, E6 and E7 peptide pools. Peptides were used at a concentration of 5 µg/ml/peptide. After 4 days of incubation at 37° C., PBMCs were harvested, washed, and seeded in four replicate wells at a density of $10^5$ cells per well in 100 µl IMDM enriched with 10% FCS in a Multiscreen 96-well plate (Millipore, Etten-Leur, The Netherlands) coated with an IFNγ catching antibody (Mabtech AB, Nacha, Sweden). Further antibody incubations and development of the ELISPOT was performed according to the manufacturer's instructions (Mabtech). Spots were counted with a fully automated computer-assisted-video-imaging analysis system (Bio Sys). Specific spots were calculated by subtracting the mean number of spots+2×SD of the medium control from the mean number of spots in experimental wells (van der Burg, 2001).

T Cell Proliferation Assay

T-cell cultures of the skin biopsies were tested for recognition of the specific peptides and protein in a 3-day proliferation assay (van der Burg, 2001). Briefly, autologous monocytes were isolated from PBMCs by adherence to a flat-bottom 96-well plate during 2 h in X-vivo 15 medium (Cambrex) at 37° C. The monocytes were used as APCs, loaded overnight with 10 mg/ml peptide and 20 mg/ml protein. Skin test-infiltrating-lymfocytes were seeded at a density of $2-5 \times 10^4$ cells/well in IMDM suplemented with 10% AB serum. Medium alone was taken along as a negative control, phytohemagglutinine (0.5 µg/ml) served as a positive control. Proliferation was measured by [$^3$H] thymidine (5 µCi/mmol) incorporation. A proliferative response was defined specific as the stimulation index (SI)≥3. Supernatants of the proliferation assays were harvested 48 hours after incubation for the analysis of antigen-specific cytokine production.

Analysis of Cytokines Associated with HPV16-Specific Proliferative Responses

The simultaneous detection of six different Th1 and Th2 cytokines: IFNγ, tumor necrosis factor α, interleukin 2 (IL2), IL4, IL5 and IL10 was performed using the cytometric bead array (Becton Dickinson) according to the manufacturer's instructions. Cut-off values were based on the standard curves of the different cytokines (100 pg/ml IFNγ and 20 pg/ml for the remaining cytokines). Antigen-specific cytokine production was defined as a cytokine concentration above cutoff level and >2× the concentration of the medium control (de Jong, 2004).

Intracellular Cytokine Staining (ICS)

The specificity and character of the T cell cultures derived from positive skin reaction sites was tested by ICS as reported previously (de Jong, 2005). Briefly, skin test infiltrating lymphocytes were harvested, washed and suspended in 1MDM+10% AB serum and $2-5 \times 10^4$ cells were added to autologous monocytes that were pulsed overnight with 50 µl peptide (10 µg/ml) or protein (20 µg/ml) in X vivo medium. Medium alone was taken along as a negative control, phytohemagglutinine (0.5 µg/ml) served as a positive control. Samples were simultaneously stained with FITC-labelled mouse-antihuman IFNγ (0.5 g/ml, BD PharMingen), PE-labelled mouse-antihuman IL5 (0.2 mg/ml, BD PharMingen), APC-labelled anti-CD4 (BD Bioscience) and PerCP-labelled anti-CD8 (BD Bioscience). After incubation at 4° C., the cells were washed, fixed with 1% paraformaldehyde and analyzed by flow cytrometry (FACSscan, BD Biosciences)

Statistical Analysis

Fisher's Exact test (2-tailed) was used to analyze the relationship between the detection of IFNγ-producing HPV-specific T-cells in PBMC, the presence of a skin test reaction or the presence of HPV-specific T-cells in skin biopsies, as well as differences between patients and healthy controls with respect to the size or the number of the skin reactions within these groups. Statistical analyzes were performed using Graphpad Instat Software (version 3.0) and Graphpad Prism 4.

Results

Skin Reactions to Intracutaneous Injection with HPV 16 E2, E6- and E7 Peptides

We studied skin reactions in both healthy subjects and patients with HPV induced disease after intracutaneous injection with HPV16 E2, -E6 and E7 peptides. Positive skin reactions appeared as flat reddish papules of 2 to 20 mm of diameter, arising within 2 to 25 days after injection. A positive skin reaction was detected in 46 of the 152 skin tests in the control group and in 30 out of 136 skin test sites in the patient group. The size of the skin reactions did not differ between the two groups. Over all, each peptide-pool in the skin test could give rise to a positive skin reaction. Most frequently reactions against $E2_{31-75}$ (10 out of 19 subjects), $E6_{37-104}$ (9/16) and $E7_{43-98}$ (7/19) were observed in the control group. This reaction pattern resembles that of what we previously observed in PBMC (de Jong, 2002; Welters, 2003), as well as the pattern observed in the patient group (FIG. 1).

The time for skin reactions to appear, differed considerably between the group of healthy volunteers and patients.

A classical DTH reaction, within 24 to 72 hours after injection, was observed in only three cases, 2 patients and 1 healthy control (FIG. 1).

The majority of skin reactions in the patient group developed within 2 to 20 days, reaching a maximum after one week (FIG. 1). Notably, 5 out of 9 patients with history of a HPV16 related disease, showed a positive reaction within 8 days. However, within the group of controls most of the skin reactions were detected between day 13-25.

Skin Reactions in Healthy Donors are Associated with Higher Frequencies of HPV 16-Specific T-Cells in the Peripheral Blood.

Figure 2:
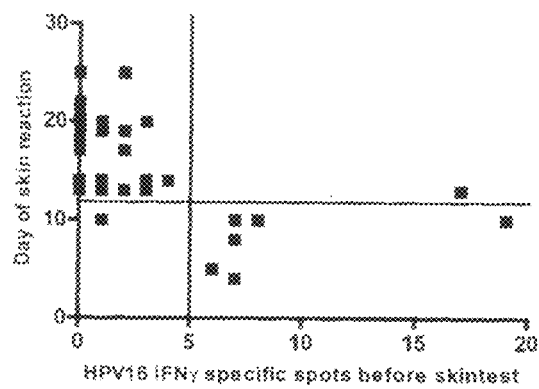

In order to compare the results of the skin test with the presence of circulating HPV16-specific type 1 T cells, an IFNγ ELIspot assay was performed with PBMC's collected before the intradermal peptide-challenge was given. In 5 out of 19 healthy volunteers we were able to detect a HPV16-specific immune response by IFM-ELIspot. The detection of ≥5 circulating HPV 16-specific T-cells per 100.000 PBMC in the pre-challenge blood sample of healthy individuals was associated with an early (≤13 days) positive skin reaction to the same peptide sequence (p=0.0003, two tailed Fisher's exact test; FIG. 2). No HPV 16-specific circulating T-cells were detected in the pre-challenge blood sample healthy donors to peptides that induced a late positive skin reaction (14 to 25 days). This suggests that the frequency of circulating antigen-specific cells determine the delay time for skin reactions to appear.

Figure 3A:
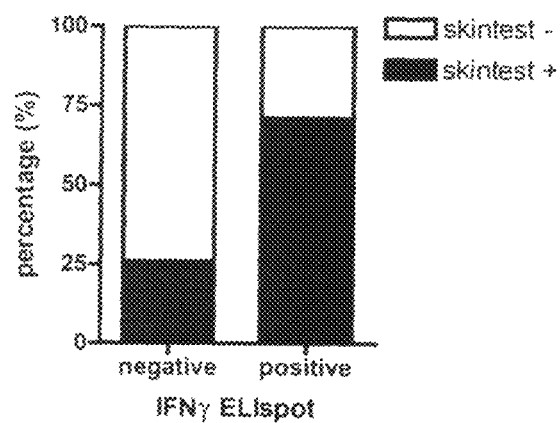

In order to assess the frequency of HPV-specific T-cells at the time that a late skin reaction appeared additional blood samples from 11 healthy volunteers were collected. In these individuals 39 out of 88 skin tests were positive. In 25 of the 39 positive skin reactions and in 10 of 49 negative skin reactions ≥5 HPV 16-specific T-cells were detected per 100.000 PBMC. At this point a significant correlation was found between the detection of circulating HPV-specific IFNγ-producing T-cells in the post-challenged blood sample and the presence of a skin reaction (p<0.0001, Fisher's exact test; FIG. 3A). This shows that the frequency of HPV16-specific T cells in the blood of healthy volunteers is significantly higher following an intradermal challenge with HPV16 peptide and indicates that intracutaneous injection of peptide antigens enhances the number of HPV16-specific T cells in the blood of healthy volunteers.

Biopsies of Positive Skin Reaction Sites Consist of Both Th1/Th2-CD4+ and CD8+ HPV16-Specific T Cells.

Approximately 25% of the positive skin reactions of healthy volunteers were not associated with the detection of HPV 16-specific IFNγ-producing T-cells in the blood, suggesting that other, non IFNγ-producing types of T-cells may infiltrate the skin after intradermal injection of HPV16 peptides.

Figure 3B:
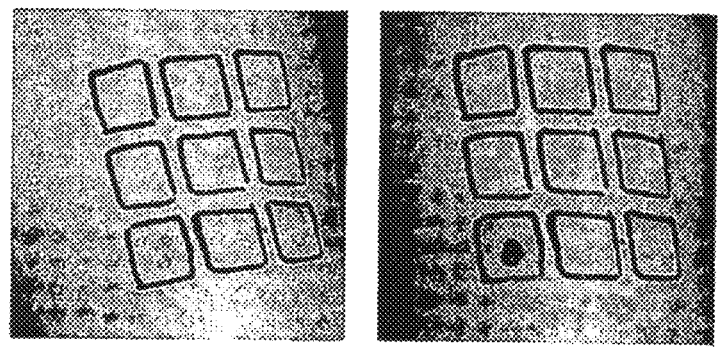
Figure 4:
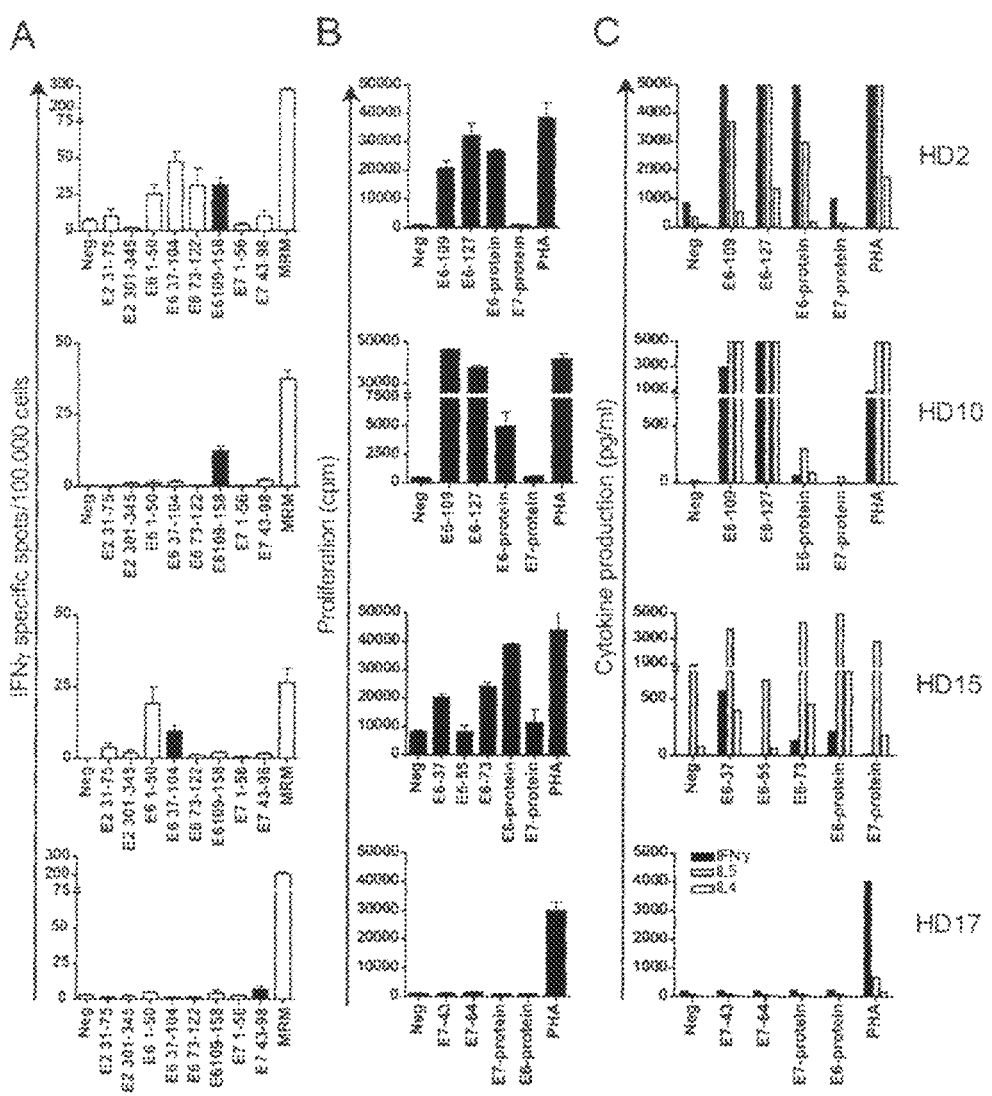

In order to characterize the cells in a positive skin reaction site punch biopsies were taken, (FIG. 3B). In total, 8 biopsies were taken from different positive skin reaction sites of 7 healthy controls and cultured with a cocktail of cytokines that allowed the outgrowth of T-cells in vitro without antigenic stimulans. In 7 of 8 cases, T-cells exfiltrated the tissue and expanded within 3-4 weeks. The expanded T-cells were tested for their specificity in a short term proliferation assay. FIG. 4 shows examples of T-cell cultures that specifically proliferated upon stimulation with autologous monocytes pulsed with the pool of peptides, also injected in this site during the skin test (HD2, HD10, HD15) as well as to monocytes pulsed with HPV16 E6 protein (FIG. 4AB). This indicates that these T-cells were capable of recognizing their cognate HLA-peptide complexes after the antigen was naturally processed and presented. Analysis of the supernatants of these proliferative T-cell cultures revealed a mixed Th1/Th2 cytokine profile in that the HPV16-specific T-cells produced IFNγ, IL-4 and IL-5 (FIG. 4C).

Figure 5:
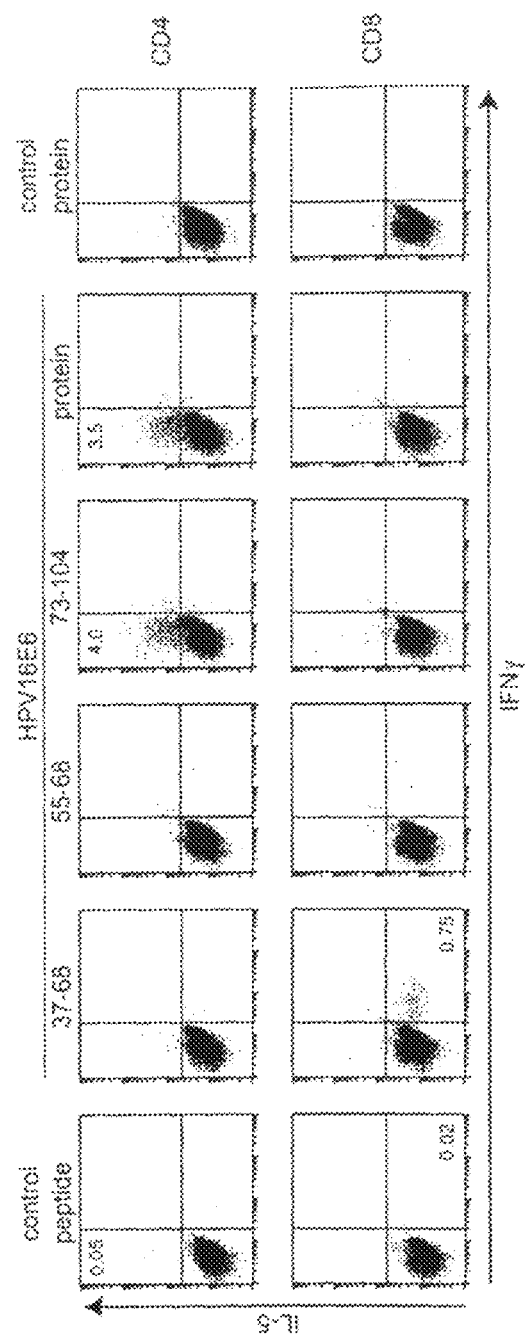

In each case that HPV-specific T-cells were detected in the biopsy culture (4 out of 8) this coincided with the detection of circulating HPV 16-specific IFNγ-producing T-cells in the post-challenge blood sample by ELIspot (compare FIGS. 4A and B). In 3 of the other 4 positive skin reaction biopsies (HD2, HD17, HD18) the T-cells did not respond to HPV16 peptides (FIG. 4; HD17) and in one case no T-cells exfiltrated the tissue at all (HD13). In these 4 cases we were not able to detect circulating HPV16-specific IFNγ-producing T-cells in the post-challenge blood sample. Co-staining of the biopsy-T cells by CD4 and CD8 cell surface markers showed that not only HPV16-specific CD4$^+$ but also HPV16-specific CD8$^+$ T cells infiltrated the skin site upon intradermal challenge with HPV16 peptide (FIG. 5). Overall, in 3 out of 4 biopsies infiltrated by HPV16-specific T-cells, we were able to detect HPV16-specific CD8$^+$ T cells.

Taken together, the population of immune cells migrating into the skin upon an intradermal challenge with HPV16 peptides comprises HPV16-specific CD4$^+$ Th1-, Th2- and CD8$^+$ cytotoxic T cells. This infiltration is paralleled by the appearance of circulating HPV 16-specific IFNγ-producing T-cells in the blood.

Discussion

Skin tests are commonly used as a simple assay for in vivo measurement of cell mediated immunity. We have validated the use of the skin test assay for the measurement of HPV16 specific cellular immune response against the early antigens E2, E6 and E7 in vivo by comparing the results with that of parallel measurements of T cell reactivity by in vitro assays.

The majority of positive skin reactions in patients with HPV related neoplasia appeared within 2-8 days after administration of the skin test similar to what was observed in CIN patients by Hopfl et al. (Hopfl, 2000). Also in the group of healthy volunteers early skin reactions appeared between 4 to 12 days after intradermal antigen challenge. In this latter group, known to display HPV16 specific type 1 T cell responses in vitro (de Jong, 2002; Welters, 2003), the appearance of an early skin reaction (within 13 days) was significantly associated with the detection of IFNγ-producing HPV16-specific T cells at a frequency of at least 1 per 20.000 PBMC (FIG. 2, p<0.001). The same cut-off criteria for a positive reaction in the IFNγ ELIspot assay are recommended by Jeffries et al (Jeffries, 2006), who used mathematical tools to define the appropriate cut-off of the ELISPOT in relation to Mantoux-tests. The low number of circulating memory T cells (FIG. 2) may explain why the skin reactions appear somewhat delayed compared to classical DTH tests. The T cells need to be boosted or reactivated and start to divide before enough cells are produced to cause a local inflammatory reaction: the positive skin test. Indeed, at the time a positive skin reaction appears, a higher frequency of HPV16-specific Th1 responses can be detected in the peripheral blood (FIG. 3).

In contrast to the healthy individuals, skin reactions in the patient population were not associated with circulating HPV16 specific type 1 T cells as measured by IFNγ ELIspot, suggesting that HPV16 specific T cells producing other cytokines than IFNγ infiltrated the skin test site in patients. Historically it has been postulated that the Th1 cell induce DTH responses, however, several studies have now shown that also Th2 cells infiltrating the skin test sites (Wang, 1999;

Woodfolk, 2001). Similarly, this study shows that the positive skin test sites of healthy volunteers contain both Th1 and Th2 type HPV 16-specific T cells (FIGS. 4 and 5). In addition, positive skin reactions may also be the result of the influx of non-specific T cells as became evident from two in depth studies of positive skin test sites used to assay the specific immune response following vaccination of patients with renal cell cancer or melanoma (Bleumer, 2007). Also this study showed that a number of positive skin test sites from healthy subjects were infiltrated with T-cells that did not respond to the injected HPV16 antigens. So far, the reason for a-specific positive skin reactions remains unclear. However, based on these results and in view of our previous studies showing that most of the cervical carcinoma patients lack functional HPV-specific CD4$^+$ T cell immunity (de Jong, 2004), we assume that the positive skin reactions in cancer patients are the result of either circulating HPV-specific non-Th1 cells or that of infiltrating T cells that are not-specific for HPV16.

Unexpectedly, we observed the majority of skin reactions in healthy individuals to appear 2 to 3 weeks after intradermal injection of the antigen. While, these late positive skin reactions were not correlated with detection of circulating HPV-specific CD4$^+$ memory T cells in pre-challenge blood (FIG. 2) the immunological constitution of these skin test sites are similar to that of classic DTH tests (Platt, 1983; Poulter, 1982) and comprised of HPV16-specific CD4$^+$ Th1- and Th2-cells as well as HPV16- specific CD8$^+$ T cells (FIGS. 4 and 5). We hypothesize that these reactions might be the result of T cell priming. This has also been noted in 29% of patients whom underwent a 2-step tuberculin skin testing protocol and whom were only positive at the second test round (Akcay, 2003). In general, vaccine-induced T cell responses peak at 10 to 14 days after vaccination and not at three weeks. However, one should bear in mind that in such protocol a higher antigen dose as well as strong adjuvants are injected. It is therefore reasonable to assume that the T cell responses induced by intradermal challenge develop more slowly and peak at a later period. Since the intra dermal peptide challenge in healthy volunteers results in the induction of both HPV16-specific CD4$^+$ and CD8$^+$ T cells it, therefore, should be considered as a single, low dose vaccination.

The main objective of this pilot study was to validate the use of the HPV16 specific skin test to detect type 1 immune responses in vivo. In healthy volunteers, a positive skin reaction within 13 days is indeed correlated with the presence of circulating IFNγ-producing memory T cells as detected by the IFNγ ELIspot in vitro. Importantly, we also observed discrepancies between the outcomes obtained by skin test and ELIspot. In a number of cases HPV 16-specific circulating IFNγ-producing T cells were detected in the post-challenge blood samples but without a concomitant skin reaction and vice versa (FIG. 3A), and this may be considered as a false negative or false positive result. In order to fully understand the impact of this on the interpretation of the detection of type 1 immunity against HPV, we have begun a field trial in a large group of patients and healthy volunteers in Indonesia.

TABLE 1

Patient characteristics

| patient | age (yrs) | diagnosis | grade/stage | Treatment | time (months)[a] | HPV |
|---|---|---|---|---|---|---|
| 1 | 72 | CxCa | IB[b] | radical hysterectomy | 9 | 16 |
| 2 | 57 | CxCa | IA | radical hysterectomy | 18 | 16 |
| 3 | 57 | CxCa | IIB | Radiotherapy | 36 | ? |
| 4 | 50 | CxCa | IB | radical hysterectomy | 6 | 16 |
| 5 | 44 | CxCa | IA | Hysterectomy | 36 | 16 |
| 6 | 53 | CxCa | IIB | chemoradiation | 36 | 16neg |
| 7 | 34 | CxCa | IB | radical hysterectomy | 48 | ? |
| 8 | 44 | CxCa | IB | radical hysterectomy | 7 | 16 |
| 9 | 43 | CxCa | IB | radical hysterectomy | 39 | 16 |
| 10 | 32 | CxCa | IA | radical hysterectomy | 20 | ? |
| 11 | 58 | CxCa | IB | radical hysterectomy | 74 | 18 |
| 12 | 44 | CxCa | IIA | radical hysterectomy | 10 | 16 |
| 13 | 28 | CIN | I | LEEP[c] | 0 | neg |
| 14 | 29 | CIN | III | LEEP | 2 | ? |
| 15 | 42 | CIN | II | LEEP | 3 | ? |
| 16 | 49 | CIN | III | LEEP | 60 | 18 |
| 17 | 44 | CIN | III | LEEP | 12 | 16 |

[a]Time of treatment before skin tests were performed
[b]cervical cancer stage according to FIGO
[c]Loop electrosurgical excision procedure

REFERENCE LIST

Akcay, A., Erdem, Y., Altun, B., Usalan, C., Agca, E., Yasavul, U., Turgan, C., and Caglar, S. The booster phenomenon in 2-step tuberculin skin testing of patients receiving long-term hemodialysis. Am. J. Infect. Control, 31: 371-374, 2003.

Alvarez D. et al, J. of Immunology, (2005), 174:1664-1674

Black, C. A. Delayed type hypersensitivity: current theories with an historic perspective. Dermatol. Online. J., 5: 7, 1999.

Bleumer, I., Tiemessen, D. M., Oosterwijk-Wakka, J. C., Voller, M. C., De Weijer, K., Mulders, P. F., and Oosterwijk, E. Preliminary analysis of patients with progressive renal cell carcinoma vaccinated with CA9-peptide-pulsed mature dendritic cells. J. Immunother., 30: 116-122, 2007.

Bontkes, H. J., de Gruijl, T. D., van den Muysenberg, A. J., Verheijen, R. H., Stukart, M. J., Meijer, C. J., Scheper, R. J., Stacey, S, N., Duggan-Keen, M. F., Stern, P. L., Man, S., Borysiewicz, L. K., and Walboomers, J. M. Human papillomavirus type 16 E6/E7-specific cytotoxic T lymphocytes in women with cervical neoplasia. Int. J. Cancer, 88: 92-98, 2000.

Bosch et al., Prevalence of human papillomavirus in cervical cancer: a worldwide perspective. International biological study on cervical cancer (IBSCC) Study Group. J Natl Cancer Inst, 87, 796-802 (1995).

Bosch, F. X., Lorincz, A., Munoz, N., Meijer, C. J., and Shah, K. V. The causal relation between human papillomavirus and cervical cancer. J. Clin. Pathol., 55: 244-265, 2002.

Burk, R. D., Kelly, P., Feldman, J., Bromberg, J., Vermund, S. H., DeHovitz, J. A., and Landesman, S. H. Declining prevalence of cervicovaginal human papillomavirus infection with age is independent of other risk factors. Sex Transm. Dis., 23: 333-341, 1996.

Dyson et al., The human papilloma virus-16 E7 oncoprotein is able to bind to the retinoblastoma gene product. Science 243 (4893): 934, 1989

Chambers, M. A., Stacey, S, N., Arrand, J. R., and Stanley, M. A. Delayed-type hypersensitivity response to human papillomavirus type 16 E6 protein in a mouse model. J. Gen. Virol., 75 (Pt 1): 165-169, 1994.

Claas, E. C., Melchers, W. J., van der Linden, H. C., Lindeman, J., and Quint, W. G. Human papillomavirus detection in paraffin-embedded cervical carcinomas and metastases of the carcinomas by the polymerase chain reaction. Am. J. Pathol., 135: 703-709, 1989.

de Jong, A., van der Burg, S. H., Kwappenberg, K. M., van der Hulst, J. M., Franken, K. L., Geluk, A., van Meijgaarden, K. E., Drijfhout, J. W., Kenter, G., Vermeij, P., Melief, C. J., and Offringa, R. Frequent detection of human papillomavirus 16 E2-specific T-helper immunity in healthy subjects. Cancer Res., 62: 472-479, 2002.

de Jong, A., van der Hulst, J. M., Kenter, G. G., Drijfhout, J. W., Franken, K. L., Vermeij, P., Offringa, R., van der Burg, S. H., and Melief, C. J. Rapid enrichment of human papillomavirus (HPV)-specific polyclonal T cell populations for adoptive immunotherapy of cervical cancer. Int. J. Cancer, 114: 274-282, 2005.

de Jong, A., van Poelgeest, M. I., van der Hulst, J. M., Drijfhout, J. W., Fleuren, G. J., Melief, C. J., Kenter, G., Offringa, R., and van der Burg, S. H. Human papillomavirus type 16-positive cervical cancer is associated with impaired CD4+ T-cell immunity against early antigens E2 and E6. Cancer Res., 64: 5449-5455, 2004.

de Vries, 1. J., Bernsen, M. R., Lesterhuis, W. J., Scharenborg, N. M., Strijk, S. P., Gerritsen, M. J., Ruiter, D. J., Figdor, C. G., Punt, C. J., and Adema, G. J. Immunomonitoring tumor-specific T cells in delayed-type hypersensitivity skin biopsies after dendritic cell vaccination correlates with clinical outcome. J. Clin. Oncol., 23: 5779-5787, 2005.

Evander, M., Edlund, K., Gustafsson, A., Jonsson, M., Karlsson, R., Rylander, E., and Wadell, G. Human papillomavirus infection is transient in young women: a population-based cohort study. J. Infect. Dis., 171: 1026-1030, 1995.

Evans, E. M., MAN, S., EVANS, A. S. AND BORYSIEWICZ, L. K., Infiltration of cervical cancer tissue with human papillomavirus-specific cytotoxic T-lymphocytes. Cancer Res., 57, 2943-2950 (1997).

Feltkamp et al., Vaccination with cytotoxic T lymphocyte epitope-containing peptide protects against a tumor induced by human papillomavirus type 16-transformed cells. Eur J Immunol 23 (9): 2242, 1993

Halpert et al., Human papillomavirus and lower genital neoplasia in renal transplant patients. Obstet Gynecol 68 (2): 251, 1986

Han et al., Protection of rabbits from viral challenge by gene gun-based intracutaneous vaccination with a combination of cottontail rabbit papillomavirus E1, E2, E6, and E7 genes. J Virol 73 (8): 7039, 1999.

Ho G Y et al., Risk of genital human papillomavirus infection in women with human immunodeficiency virus-induced immunosuppression. Int J Cancer 56 (6):788, 1994

Ho, G. Y., Bierman, R., Beardsley, L., Chang, C. J., and Burk, R. D. Natural history of cervicovaginal papillomavirus infection in young women. N. Engl. J. Med., 338: 423-428, 1998.

Hopfl, R. M., Christensen, N. D., Angell, M. G., and Kreider, J. W. Skin test to assess immunity against cottontail rabbit papillomavirus antigens in rabbits with progressing papillomas or after papilloma regression. J. Invest Dermatol., 101: 227-231, 1993.

Hopfl, R., Heim, K., Christensen, N., Zumbach, K., Wieland, U., Volgger, B., Widschwendtcr, A., Haimbuchner, S., Muller-Holzner, E., Pawlita, M., Pfister, H., and Fritsch, P. Spontaneous regression of CIN and delayed-type hypersensitivity to HPV-16 oncoprotein E7. Lancet, 356: 1985-1986, 2000.

Hopfl, R., Sandbichler, M., Sepp, N., Heim, K., Muller-Holzner, E., Wartusch, B., Dapunt, 0., Jochmus-Kudielka, I., ter Meulen, J., Gissmann, L., and . Skin test for HPV type 16 proteins in cervical intraepithelial neoplasia. Lancet, 337: 373-374, 1991.

Huebner, R. E., Schein, M. F., and Bass, J. B., Jr. The tuberculin skin test. Clin. Infect. Dis., 17: 968-975, 1993.

Jaeger, E., Bernhard, H., Romero, P., Ringhoffer, M., Arand, M., Karbach, J., Ilsemann, C., Hagedorn, M., and Knuth, A. Generation of cytotoxic T-cell responses with synthetic melanoma-associated peptides in vivo: implications for tumor vaccines with melanoma-associated antigens. Int. J. Cancer, 66: 162-169, 1996.

Jeffries, D. J., Hill, P. C., Fox, A., Lugos, M., Jackson-Sillah, D. J., Adegbola, R. A., and Brookes, R. H. Identifying ELISPOT and skin test cut-offs for diagnosis of *Mycobacterium tuberculosis* infection in The Gambia. Int. J. Tuberc. Lung Dis., 10: 192-198, 2006.

Jenkins, D., Sherlaw-Johnson, C., and Gallivan, S. Can papilloma virus testing be used to improve cervical cancer screening? Int. J. Cancer, 65: 768-773, 1996.

Jondal et al., MHC class 1-restricted CTL responses to exogenous antigens. Immunity 5 (4): 295, 1996

Karlsson, R., Jonsson, M., Edlund, K., Evander, M., Gustaysson, A., Boden, E., Rylander, E., and Wadell, G. Lifetime number of partners as the only independent risk factor for human papillomavirus infection: a population-based study. Sex Transm. Dis., 22: 119-127, 1995.

Kast et al., Protection against lethal Sendai virus infection by in vivo priming of virus specific cytotoxic T lymphocytes with a free synthetic peptide. Proc. Natl. Acad. Sci. U.S.A.88 (6): 2283, 1991

Kjaer, S. K., van den Brule, A. J., Paull, G., Svare, E. I., Sherman, M. E., Thomsen, B. L., Suntum, M., Bock, J. E., Poll, P. A., and Meijer, C. J. Type specific persistence of high risk human papillomavirus (HPV) as indicator of high grade cervical squamous intraepithelial lesions in young women: population based prospective follow up study. BMJ, 325: 572, 2002.

Koutsky Epidemiology of genital human papillomavirus infection. Am J Med 102. (5A): 3, 1997.

Kurts et al., CD4+ T cell help impairs CD8+ T cell deletion induced by cross-presentation of self antigens and favors autoimmunity. J Exp Med 186 (12): 2057, 1997

Marrazzo et al., Genital human papillomavirus infection in women who have sex with women: a review. Am J Obstet Gynecol 183 (3): 770, 2000

Matorras et al., Human immunodeficiency virus-induced immunosuppression: a risk factor for human papillomavirus infection. Am J Obstet Gynecol 164(1 Pt 1): 42, 1991

Melief et al., Strategies for Immunotherapy of Cancer. Adv. Immunol., 75, 235-281 (2000).

Munoz, N., Bosch, F. X., de Sanjose, S., Herrero, R., Castellsague, X., Shah, K. V., Snijders, P. J., and Meijer, C. J. Epidemiologic classification of human papillomavirus types associated with cervical cancer. N. Engl. J. Med., 348: 518-527, 2003.

Nakagawa, M., Stites, D. P., Farhat, S., Sisler, J. R., Moss, B., Kong, F., Moscicki, A. B., and Palefsky, J. M. Cytotoxic T lymphocyte responses to E6 and E7 proteins of human papillomavirus type 16: relationship to cervical intraepithelial neoplasia. J. Infect. Dis., 175: 927-931, 1997.

Nijman, H. W., Offringa, R., and van der Burg, S. H. Distinct regulation and impact of type 1 T-cell immunity against HPV16 L1, E2 and E6 antigens during HPV16-induced cervical infection and neoplasia. Int. J. Cancer, 118: 675-683, 2006.

Nimako et al., Human papillomavirus-specific cytotoxic T lymphocytes in patients with cervical intraepithelial neoplasia grade 111. Cancer Res., 57, 4855-4861 (1997).

Nimako, M., Fiander, A. N., Wilkinson, G. W., Borysiewicz, L. K., and Man, S. Human papillomavirus-specific cytotoxic T lymphocytes in patients with cervical intraepithelial neoplasia grade III. Cancer Res., 57: 4855-4861, 1997.

Ossendorp et al., Specific T helper cell requirement for optimal induction of cytotoxic T lymphocytes against major histocompatibility complex class II negative tumors. J. Exp. Med. 187 (5): 1, 1998.

Ozsaran, A. A., Ates, T., Dikmen, Y., Zeytinoglu, A., Terek, C., Erhan, Y., Ozacar, T., and Bilgic, A. Evaluation of the risk of cervical intraepithelial neoplasia and human papilloma virus infection in renal transplant patients receiving immunosuppressive therapy. Eur. J. Gynaecol. Oncol., 20: 127-130, 1999.

Pardoll et al., The role of CD4+ T cell responses in antitumor immunity. Curr. Opin. Immunol., 10, 588-94 (1998).

Platt, J. L., Grant, B. W., Eddy, A. A., and Michael, A. F. Immune cell populations in cutaneous delayed-type hypersensitivity. J. Exp. Med., 158: 1227-1242, 1983.

Poulter, L. W., Seymour, G. J., Duke, 0., Janossy, G., and Panayi, G. Immunohistological analysis of delayed-type hypersensitivity in man. Cell Immunol., 74: 358-369, 1982.

Reimann et al., Alternative antigen processing pathways in anti-infective immunity. Curr Opin Immunol 9 (4): 462, 1997

Ressing et al., Human CTL epitopes encoded by human papillomavirus type 16 E6 and E7 identified through in vivo and in vitro immunogenicity studies of HLA-A*0201 binding peptides. J. Immunol., 154, 59345943 (1995).

Ressing et al., Detection of T helper responses, but not of human papillomavirus-specific cytotoxic T lymphocyte responses, after peptide vaccination of patients with cervical carcinoma. J. Immunother., 23, 25566 (2000).

Ressing et al., Occasional memory cytotoxic T-cell responses of patients with human papillomavirus type 16-positive cervical lesions against a human leukocyte antigen-A*0201-restricted E7-encoded epitope. Cancer Res., 56, 582-588 (1996).

Remmink, A. J., Walboomers, J. M., Helmerhorst, T. J., Voorhorst, F. J., Rozendaal, L., Risse, E. K., Meijer, C. J., and Kenemans, P. The presence of persistent high-risk HPV genotypes in dysplastic cervical lesions is associated with progressive disease: natural history up to 36 months. Int. J. Cancer, 61: 306-311, 1995.

Rieser, C., Ramoner, R., Holtl, L., Rogatsch, H., Papesh, C., Stenzl, A., Bartsch, G., and Thurnher, M. Mature dendritic cells induce T-helper type-1-dominant immune responses in patients with metastatic renal cell carcinoma. Urol. Int., 63: 151-159, 1999.

Romani N. et al, Springer Semin Immunopathol., (1992), 13:265-279.

Schoenberger et al., T-cell help for cytotoxic T lymphocytes is mediated by CD40-CD40L interactions. Nature 393 (6684): 480, 1998.

Selvakumar et al., Immunization with nonstructural proteins E1 and E2 of cottontail rabbit papillomavirus stimulates regression of virus-induced papillomas. J Virol 69(1): 602, 1995.

Sscheffner et al., The E6oncoprotein encoded by human papillomavirus types 16 and 18 promotes the degradation of p53. Cell 63 (6): 1129, 1990.

Sun, X. W., Kuhn, L., Ellerbrock, T. V., Chiasson, M. A., Bush, T. J., and Wright, T. C., Jr. Human papillomavirus infection in women infected with the human immunodeficiency virus. N. Engl. J. Med., 337: 1343-1349, 1997.

Thomas-Kaskel, A. K., Zeiser, R., Jochim, R., Robbel, C., Schultze-Seemann, W., Waller, C. F., and Veelken, H. Vaccination of advanced prostate cancer patients with PSCA and PSA peptide-loaded dendritic cells induces DTH responses that correlate with superior overall survival. Int. J. Cancer, 119: 2428-2434, 2006.

Toes et al., Peptide vaccination can lead to enhanced tumor growth through specific T-cell tolerance induction. Proc Natl Acad Sci USA 93 (15):7855, 1996a.

Toes et al., Enhanced tumor outgrowth after peptide vaccination. Functional deletion of tumor-specific CTL induced by peptide vaccination can lead to the inability to reject tumors. J Immunol 156 (10): 3911, 1996b Toes et al., CD4 T cells and their role in antitumor immune responses. J. Exp. Med., 189, 753-756 (1999).

Turk, J. L. Delayed hypersensitivity. 2nd ed. 1975. Amsterdam, Elsevier. Ref Type: Generic Vambutas, A., DeVoti, J., Nouri, M., Drijfhout, J. W., Lipford, G. B., Bonagura, V. R., van der Burg, S. H., and Melief, C. J. Therapeutic vaccination with papillomavirus E6 and E7 long peptides results in the control of both established virus-induced lesions and latently infected sites in a pre-clinical cottontail rabbit papillomavirus model. Vaccine, 23: 5271-5280, 2005.

van der Burg, S. H., Kwappenberg, K. M., Geluk, A., van der, K. M., Pontesilli, O., Hovenkamp, E., Franken, K. L., van Meijgaarden, K. E., Drijfhout, J. W., Ottenhoff, T. H., Melief, C. J., and Offringa, R. Identification of a conserved universal Th epitope in HIV-1 reverse transcriptase that is processed and presented to HIV-specific CD4+ T cells by at least four unrelated HLA-DR molecules. J. Immunol., 162: 152-160, 1999.

van der Burg, S. H., Ressing, M. E., Kwappenberg, K. M., de Jong, A., Straathof, K., de Jong, J., Geluk, A., van Meijgaarden, K. E., Franken, K. L., Ottenhoff, T. H., Fleuren, G. J., Kenter, G., Melief, C. J., and Offringa, R. Natural T-helper immunity against human papillomavirus type 16 (HPV16) E7-derived peptide epitopes in patients with HPV16-positive cervical lesions: identification of 3 human leukocyte antigen class II-restricted epitopes. Int. J. Cancer, 91: 612-618, 2001.

van Poelgeest, M. I., Nijhuis, E. R., Kwappenberg, K. M., Hamming, I. E., Wouter, D. J., Fleuren, G. J., van der Zee, A. G., Melief, C. J., Kenter, G. G., Welters, M. J., de Jong, A., van den Eeden, S. J., van der Hulst, J. M., Kwappenberg, K. M., Hassane, S., Franken, K. L., Drijfhout, J. W., Fleuren, G. J., Kenter, G., Melief, C. J., Offringa, R., and van der Burg, S. H. Frequent display of human papillomavirus type 16 E6-specific memory t-Helper cells in the healthy population as witness of previous viral encounter. Cancer Res., 63: 636-641, 2003.

Vulcmanovic-Stejic, M., Reed, J. R., Lacy, K. E., Rustin, M. H., and Akbar, A. N. Mantoux Test as a model for a secondary immune response in humans. Immunol. Lett., 107: 93-101, 2006.

Wang, S., Fan, Y., Brunham, R. C., and Yang, X. IFN-gamma knockout mice show Th2-associated delayed-type hypersensitivity and the inflammatory cells fail to localize and control chlamydial infection. Eur. J. Immunol., 29: 3782-3792, 1999.

Woodfolk, J. A. and Platts-Mills, T. A. Diversity of the human allergen-specific T cell repertoire associated with distinct skin test reactions: delayed-type hypersensitivity-associated major epitopes induce Th1- and Th2-dominated responses. J. Immunol., 167: 5412-5419, 2001.

Youde, S. J., Dunbar, P. R., Evans, E. M., Fiander, A. N., Borysiewicz, L. K., Cerundolo, V., and Man, S. Use of fluorogenic histocompatibility leukocyte antigen-A*0201/HPV 16 E7 peptide complexes to isolate rare human cytotoxic T-lymphocyte-recognizing endogenous human papillomavirus antigens. Cancer Res., 60: 365-371, 2000.

Zur Hausen Papillomavirus infections-a major cause of human cancers. Biochimica et Biophysica Acta 1288: F55, 1996.

---

The invention claimed is:

1. A method for treatment of an HPV-induced intraepithelial neoplasia or cancer selected from a Human Papilloma Virus (HPV) infection, an HPV associated malignancy, a Cervical Intra-epithelial Neoplasia (CIN), a vulva Intra-epithelial Neoplasia (VIN), an Anal Intra-epithelial Neoplasia (AIN), a Vaginal Intra-epithelial Neoplasia (VAIN), a Penile Intra-epithelial Neoplasia (PIN), a cervical cancer, a vulva cancer, an anal cancer, a vaginal cancer, a head and neck cancer or a penile cancer, in a human in need thereof, the method comprising administering intradermally to said human a composition comprising a pool of the following peptides:

(i) a peptide comprising SEQ ID NO: 7 and a peptide comprising SEQ ID NO: 8;
(ii) a peptide comprising SEQ ID NO: 9 and a peptide comprising SEQ ID NO: 10;
(iii) a peptide comprising SEQ ID NO: 11 and a peptide comprising SEQ ID NO: 12;
(iv) a peptide comprising SEQ ID NO: 13, a peptide comprising SEQ ID NO: 14, and a peptide comprising SEQ ID NO: 15;
(v) a peptide comprising SEQ ID NO: 16 and a peptide comprising SEQ ID NO: 17;
(vi) a peptide comprising SEQ ID NO: 18 and a peptide comprising SEQ ID NO: 19; and/or, (vii) a combination thereof, wherein the peptides are of 22-45 contiguous amino acids of HPV-E2 or -E6 proteins and are administered in an amount suitable to elicit an antigen specific systemic cellular immune response with respect to the peptides, wherein the composition does not comprise an adjuvant, and wherein the administering treats the HPV-induced intraepithelial neoplasia or cancer.

2. The method of claim 1, wherein the peptides are of 22-40, 22-35, 22, 25, 28, 32 or 35 amino acids in length.

3. The method of claim 1, wherein the composition further comprises a contiguous amino acid sequence from HPV-E7 protein.

4. The method of claim 1, wherein the composition consists of the pool and an inert pharmaceutically acceptable carrier.

5. The method of claim 1, wherein the composition is intradermally administered directly at the site of the lesion.

6. The method of claim 1, further comprising a second composition comprising a peptide derived from HPV-E2, -E6 and/or -E7 protein, wherein the second composition is administered subcutaneously.

7. The method of claim 1, wherein said antigen specific systemic immune response comprises circulation of antigen specific T cells through the secondary lymph system of said subject.

8. The method of claim 1, wherein said antigen specific systemic immune response comprises circulation of antigen specific T cells in the peripheral blood of said subject.

9. The method of claim 1, wherein the composition comprises an additional peptide comprising any of the sequences of SEQ ID NO: 7-23.

10. The method of claim 3, wherein the composition comprises contiguous amino acid sequences from each of HPV-E2, -E6 and -E7 proteins.

11. The method according to claim 3, wherein the contiguous amino acid sequence from the HPV-E7 protein comprises any one of SEQ ID NOS: 20-23.

12. The method according to claim 3, wherein the composition is a buffered aqueous solution.

* * * * *